(12) United States Patent
Ormeci Beckers

(10) Patent No.: US 10,545,088 B2
(45) Date of Patent: Jan. 28, 2020

(54) MEASUREMENT OF TREATMENT AGENT IN A PROCESS STREAM USING ULTRAVIOLET-VISIBLE (UV-VIS) SPECTROSCOPY, AND RELATED SYSTEMS AND PROCESSES

(71) Applicant: Banu Ormeci Beckers, Manotick (CA)

(72) Inventor: Banu Ormeci Beckers, Manotick (CA)

( * ) Notice: Subject to any disclaimer, the term of this patent is extended or adjusted under 35 U.S.C. 154(b) by 807 days.

(21) Appl. No.: 14/386,388

(22) PCT Filed: Mar. 15, 2013

(86) PCT No.: PCT/CA2013/050216
§ 371 (c)(1),
(2) Date: Sep. 19, 2014

(87) PCT Pub. No.: WO2013/138929
PCT Pub. Date: Sep. 26, 2013

(65) Prior Publication Data
US 2015/0068981 A1    Mar. 12, 2015

Related U.S. Application Data

(60) Provisional application No. 61/612,923, filed on Mar. 19, 2012.

(51) Int. Cl.
| | |
|---|---|
| *G01N 21/33* | (2006.01) |
| *G01N 21/59* | (2006.01) |
| *C02F 1/52* | (2006.01) |
| *G01J 3/42* | (2006.01) |
| *C02F 1/00* | (2006.01) |

(Continued)

(52) U.S. Cl.
CPC ............. *G01N 21/33* (2013.01); *C02F 1/008* (2013.01); *C02F 1/5209* (2013.01); *G01N 21/59* (2013.01); *C02F 2209/00* (2013.01); *G01J 3/42* (2013.01); *G01N 2201/105* (2013.01)

(58) Field of Classification Search
None
See application file for complete search history.

(56) References Cited

U.S. PATENT DOCUMENTS

| | | | | |
|---|---|---|---|---|
| 4,336,141 A | * | 6/1982 | Santora .................. | B01D 17/02 210/694 |
| 5,242,602 A | * | 9/1993 | Richardson ............ | G01N 21/31 210/143 |

(Continued)

FOREIGN PATENT DOCUMENTS

| | | |
|---|---|---|
| DE | 3103126 A1 | 10/1982 |
| JP | 2002136809 A | 5/2002 |
| JP | 2008068199 A | 3/2008 |

OTHER PUBLICATIONS

Bolto et al. (Water Research, 2007, 41, 2301-2324.*

(Continued)

*Primary Examiner* — Clare M Perrin
(74) *Attorney, Agent, or Firm* — Maier & Maier, PLLC

(57) ABSTRACT

The present application provides a method of detecting an amount of a treatment agent, such as a flocculating agent, in a process stream comprising the step of measuring at least one absorption property of a sample obtained from the process stream at a wavelength of less than about 250 nm. Processes and systems for monitoring and regulating addition of treatment agents to process streams are also provided.

11 Claims, 27 Drawing Sheets

(51) Int. Cl.
  *C02F 103/30* (2006.01)
  *C02F 103/32* (2006.01)
  *C02F 103/06* (2006.01)
  *C02F 1/56* (2006.01)

(56) References Cited

U.S. PATENT DOCUMENTS

| 5,550,630 | A | | 8/1996 | Chrastil | |
|---|---|---|---|---|---|
| 5,879,564 | A | | 3/1999 | Farinato | |
| 6,120,690 | A | * | 9/2000 | Haase | C02F 1/5245 210/728 |
| 6,134,952 | A | * | 10/2000 | Garver | G01N 21/314 162/49 |
| 2002/0030012 | A1 | | 3/2002 | Sullivan et al. | |

OTHER PUBLICATIONS

Australian Office Action dated Feb. 23, 2016, in connection with corresponding AU Application No. 2013234794 (3 pgs.).
Chinese Office Action dated May 3, 2016, in connection with corresponding CN Application No. 201380024642.9 (25 pgs., including English translation).
Joep van den Broeke, et al., "On-line and in-situ UV/vis spectroscopy for multi-parameter measurements: a brief review", in SpectroscopyEUROPE, vol. 18, No. 4, 2006, pp. 1-4 (4 pgs).
Barbara H. Stuart; Polymer Analysis; John Wiley & Sons, Ltd.; University of Technology, Sydney, Australia; 41 pgs, Only pp. vi and 52-55 were provided and considered.
Joep van den Broeke et al; On-Line and In-Situ UV/vis Spectroscopy for Multi-Parameter Measurements; A Brief Review; vol. 18, No. 4 (2006); 4 pgs.
Olivier Thomas et al.; UV Spectrophotometry as a Non-Parametric Measurement of Water and Wastewater Quality Variability; Water Qual. Res. J. Canada 2005; vol. 40, No. 1; pp. 51-58.
J. van den Broeke et al; Use of In-Situ UV/vis Spectrometry in Water Monitoring in Vienna; 2008; 17 pgs.
Xin-Sheng Chai et al.; UV Spectroscopic Monitoring Method for Real-Time Wet-End Control of Polymeric Adsorption in Aqueous Fibrous Suspensions; J. Ind. Eng. Chem., vol. 13, No. 2; (2007) pp. 244-249.
International Search Report and Written Opinion dated Jun. 25, 2013 from corresponding International Application No. PCT/CA2013/050216; 9 pgs.
Notification of Transmittal of International Preliminary Report on Patentability; dated Jul. 11, 2014 and the Corrected Version of the International Preliminary Report on Patentability dated Jul. 11, 2014.
Extended European Search Report dated Sep. 7, 2015, including a Supplemental European Search Report and the European Search Opinion, in connection with EP Application No. 13763725.2 (8 pgs).
Paul A. Chadik, et al., "Removing trihalomethane precursors from various natural waters by metal coagulants", in American Water Works Association, vol. 75, No. 10, Oct. 1983, pp. 532-536 (6 pgs.).

Steven K. Dentel, et al., "Analysis and Fate of Polymers in Wastewater Treatment", in Final Report, Water Environment Research Foundation, Collection and Treatment, Project 94-REM-2, Department of Civil and Environmental Engineering, University of Delaware, 2000, 146 pgs.
European Office Action dated Mar. 27, 2017, in connection with corresponding EP Application No. 13 763 725.2 (7 pgs.).
Lin-Li Chang, et al., "NMR spectroscopy for determination of cationic polymer concentrations", in Water Research, vol. 36, 2002, pp. 2255-2264 (10 pgs.).
N.S.C. Becker, et al., "Detection of polyelectrolytes at trace levels in water by fluorescent tagging", in Reactive & Functional Polymers, vol. 60, 2004, pp. 183-193 (11 pgs.).
Brian A. Bolto, "Soluble Polymers in Water Purification", in Prog. Polym. Sci., vol. 20, 1995, pp. 987-1041 (55 pgs.).
Srinivasarao Chitikela, et al., "Dual-chemical conditioning and dewatering of anaerobically digested biosolids: laboratory evaluations", in Water Environment Research, vol. 70, No. 5, 1998, pp. 1062-1069 (8 pgs.).
Mohammad M. Abu-Orf, et al., "Centrate viscosity for continuous monitoring of polymer feed in dewatering applications", in Advances in Environmental Research, vol. 7, 2003, pp. 687-694 (8 pgs.).
Steven K. Dentel, et al., "Laboratory and Full-Scale Studies of Liquid Stream Viscosity and Streaming Current for Characterization and Monitoring of Dewaterability", in Water Research, vol. 29, No. 12, 1995, pp. 2663-2672 (10 pgs.).
Helen E. Keenan, et al., "Measurement of Polymer Residuals in an Alum Sludge", in Water Research, vol. 32, No. 10, 1998, pp. 3173-3176 (4 pgs.).
R. Gehr, et al., "The Effects of Short-Term Storage and Elevated Temperatures on the Flocculation Activity of Aqueous Polymer Solutions", in Water Pollution Research J. Canada, vol. 18, 1983, pp. 23-43 (21 pgs.).
Mohammad M. Abu-Orf, et al., "Polymer dose assessment using the streaming current detector", in Water Environment Research, vol. 69, 1997, pp. 1075-1085 (11 pgs.).
Seokjong Byun, et al., "Automatic control of polymer dosage using streaming potential for waterworks sludge conditioning", in ScienceDirect—Separation and Purification Technology, vol. 57, 2007, pp. 230-236 (7 pgs.).
O. Kammona, et al., "Recent Developments in Hardware Sensors for the On-Line Monitoring of Polymerization Reactions", in Journal of Macromolecular Science, Part C, vol. 39, No. 1, 1999, pp. 57-134 (80 pgs.).
Office Action dated Sep. 3, 2018 in corresponding European Application No. 13 763 725.2; 5 pages.
Ozaki, Y. et al., "Far-Ultraviolet Spectroscopy in the Solid and Liquid States: A Review", Applied Spectroscopy, Jan. 1, 2012, vol. 66, Issue 1, pp. 1-25.
Office Action dated Jan. 24, 2019 in corresponding European Application No. 13 763 725.2; 5 pages.
Office Action dated Jan. 29, 2019 in corresponding Canadian Application No. 2,867,779; 3 pages.

* cited by examiner

MEASUREMENT OF TREATMENT AGENT IN A PROCESS STREAM USING ULTRAVIOLET-VISIBLE (UV-VIS) SPECTROSCOPY, AND RELATED SYSTEMS AND PROCESSES

This patent application claims priority to U.S. Provisional Patent Application No. 61/612,923, filed Mar. 19, 2012, incorporated herein in its entirety.

FIELD OF THE INVENTION

The present application pertains to the treatment of process streams, such as those originating from industrial or treatment processes. More particularly, the present application relates to methods for detecting amounts of a treatment agent in a process stream, and processes and systems for monitoring, regulating, and/or optimizing the amount of treatment agent added to the process stream.

INTRODUCTION

The use of polymers is an important, though costly, part of the sludge dewatering process during water and wastewater treatment. Large quantities of water-soluble polymers are used for water and wastewater treatment in treatment plants around the world (Chang et al., 2002). Polymers are required in wastewater treatment to improve the efficiency of sludge thickening and dewatering, and in drinking water treatment as flocculants to remove suspended solids (Chadik and Amy 1983; Bolto, 1995).

Synthetic polymers can increase the size and strength of flocs formed by alum or iron-based coagulants (Becker et al., 2004). Moreover, they can replace inorganic coagulants with significant improvement on filter run times and sludge quantities. Synthetic polymers also substantially reduce the volume of solids generated and result in important savings in sludge handling and disposal costs.

Analytical methods that are available for the measurement of polymers are complex and require advanced research instruments, trained personnel, and pretreatment and processing of samples that may take several days. Simpler methods such as those that rely on colorimetric methods, titration, turbidity and viscosity lack the specificity and sensitivity particularly at low polymer concentrations. Therefore, neither the advanced nor the simpler methods are suitable for practical applications in the field of process optimization. There is also no available method that can be used in-line and that can provide real-time information on measured polymer concentrations, which would be very valuable for industrial applications. In addition, in some cases, it is also necessary to measure the residual polymer concentration in effluents before discharge to the environment, and this has been a main challenge particularly for effluents containing low polymer concentrations (0-10 mg/L). Overall, a simple and sensitive method for determining polymer concentrations in water and water-based slurries is currently lacking.

Polymers can account for the largest portion of the operating and maintenance cost in biosolids management (Chitikela and Dentel, 1998), and as such, it is important to use polymers in the most cost effective manner. In addition to the unnecessary cost of using excess polymer during sludge dewatering, both under- or over-dosing with the polymer will lead to a less-than-optimal dewatered sludge, increasing the cost of disposal of the treated sludge. Therefore, it is important to use polymers at their optimum dose. This ideally requires the ability to measure and adjust the polymer dose in-line and real-time.

While it is easy to determine the optimal dose for a digested sludge using a jar test apparatus, this test takes time to perform, and the optimal polymer dose may change on an hourly basis depending on the characteristics of the wastewater treatment plant (WWTP) influent (Abu-Orf et al., 2003). Using the filtrate or centrate from a sludge dewatering system as an indicator of solids dewatering effectiveness allows for a reliable continuous sampling protocol and measurement collection mechanism (Dentel and Abu-Orf, 1995). When optimum polymer dose is exceeded during conditioning, an increase in the residual polymer concentration is expected in the sludge centrate or filtrate during dewatering.

A simple tool for detecting residual polymer concentrations in centrate or filtrate is currently lacking. Such a tool could ideally be used in-line, so that operators would be able to easily identify when there is an excess of polymer in the centrate or filtrate from the sludge dewatering system. Chang et al. (2002) used nuclear magnetic resonance (NMR) to measure polymer concentrations in filtrate samples, and reported that the residual polymer concentration was approximately 8 mg/L in a belt press filtrate sample. The same filtrate was also analyzed using viscosity measurement and colloid titration, and the residual polymer concentrations were measured as 1.18 and 0.11 mg/L respectively. The recovery of the NMR method was concluded to be higher than the recovery of the other methods. While robust, the NMR procedure is not practical for use as an in-line method at a wastewater treatment plant, as NMR is a highly specialized technique requiring specialized equipment and is not practical for use outside of research facilities.

Several researchers have used chromatography for the identification of residual polymer in drinking water samples or drinking water sludges. Keenan et al. (1998) and Becker et al. (2004) used size exclusion chromatography (SEC) to measure polymer residual in different drinking water samples. Concentrations of 0-10 mg/L were found with increasing polymer doses in an alum sludge, and the detection limit for the SEC method of polymer in nanopure water was approximately 20 µg/L, while in alum sludge supernatant the detection limit was found to be approximately 66 µg/L (Keenan et al., 1998). Using fluorescence and tagging of polyelectrolytes, Becker et al. (2004) achieved a detection limit of approximately 10 µg/L for polymer in purified water after tagging; however, the detection limit for polyelectrolytes increased to >100 µg/L for water from a drinking water reservoir. Dentel et al. (2000) used gel permeation chromatography to measure polymer residual in wastewater treatment applications, and reported that the results were difficult to reproduce and the method was not suited to complex environmental samples without further work.

Gehr et al. (1983) used colloid titration and test suspension methods to measure residual polymer in filtrate from a belt filter press at a sewage treatment plant. Concentrations of 0.6 mg/L (using colloid titration) and 0.1 mg/L (using test suspension) were found for the same polymer. Chang et al. (2002) evaluated both of these methods against the previously-mentioned NMR method and found that colloid titration and test suspension methods underreported the amount of residual polymer present in the water sample.

Several indirect methods for polymer residual detection and analysis have also been used, including streaming current detection (Abu-Orf and Dentel 1997), viscosity (Abu-Orf et al., 2003), and streaming potential (Byun et al., 2007). In some cases, i.e., viscosity measurements on centrate, the equipment necessary to provide analysis has not been designed for use in a wastewater treatment facility, and challenges exist in terms of implementation of these technologies at the full scale (Abu-Orf et al., 2003).

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

In one aspect of the present application, there is provided a method of detecting an amount of flocculating agent in a process stream comprising the step of measuring at least one absorption property of a sample obtained from the process stream at a wavelength of less than about 250 nm.

In another aspect of the present application, there is provided a process for regulating an amount of a treatment agent added to a process stream comprising:
(i) measuring at least one absorption property of a sample obtained from the process stream at a wavelength of less than about 250 nm;
(ii) comparing the measured at least one absorption property to a preselected value that corresponds with a desired concentration of the treatment agent; and
(iii)(a) adjusting the amount of treatment agent added to the process stream if the measured at least one absorption property is outside a predetermined range around the preselected value, and
(b) repeating steps (i), (ii) and (iii)(a) until the measured at least one absorption property of the sample is within a predetermined range around the preselected value, and thereafter maintaining the amount of treatment agent added to the process stream; or
(iv) maintaining the amount of treatment agent added to the process stream if the measured at least one absorption property is within a predetermined range around the preselected value.

In yet another aspect of the present application, there is provided a system for regulating or optimizing an amount of a treatment agent added to a process stream, the system comprising means for performing the above process.

In still yet another aspect of the present application, there is provided a system for adding a treatment agent to a process stream comprising:
a treatment agent source for supplying an amount of a treatment agent to the process stream;
a sensor for measuring at least one absorption property of a sample obtained from the process stream at a wavelength of less than about 250 nm; and
a controller in communication with the sensor and the treatment agent source, wherein the controller:
compares the measured at least one absorption property to a preselected value that corresponds with a desired concentration of the treatment agent;
determines whether or not the amount of the treatment agent supplied to the process stream should be adjusted; and
adjusts the amount of the treatment agent supplied to the process stream if the measured at least one absorption property is outside a predetermined range around the preselected value, or maintains the amount of treatment agent supplied to the process stream if the measured at least one absorption property is within a predetermined range around the preselected value.

In yet another aspect of the present application, there is provided a process for monitoring an amount of a treatment agent added to a process stream comprising:
(i) measuring at least one absorption property of a monitoring sample obtained from the process stream at a wavelength of less than about 250 nm;
(ii) comparing the measured at least one absorption property to a preselected value that corresponds with a desired concentration of the treatment agent; and
(iii) generating a signal if the measured at least one absorption property is outside a predetermined range around the preselected value.

In still yet another aspect of the present application, there is provided a system for monitoring an amount of a treatment agent added to a process stream comprising:
a sensor for measuring at least one absorption property of a sample obtained from the process stream at a wavelength of less than about 250 nm;
means for comparing the measured at least one absorption property to a preselected value that corresponds with a desired concentration of the treatment agent; and
means for generating a signal if the measured at least one absorption property is outside a predetermined range around the preselected value.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Definitions

Figure 1A:
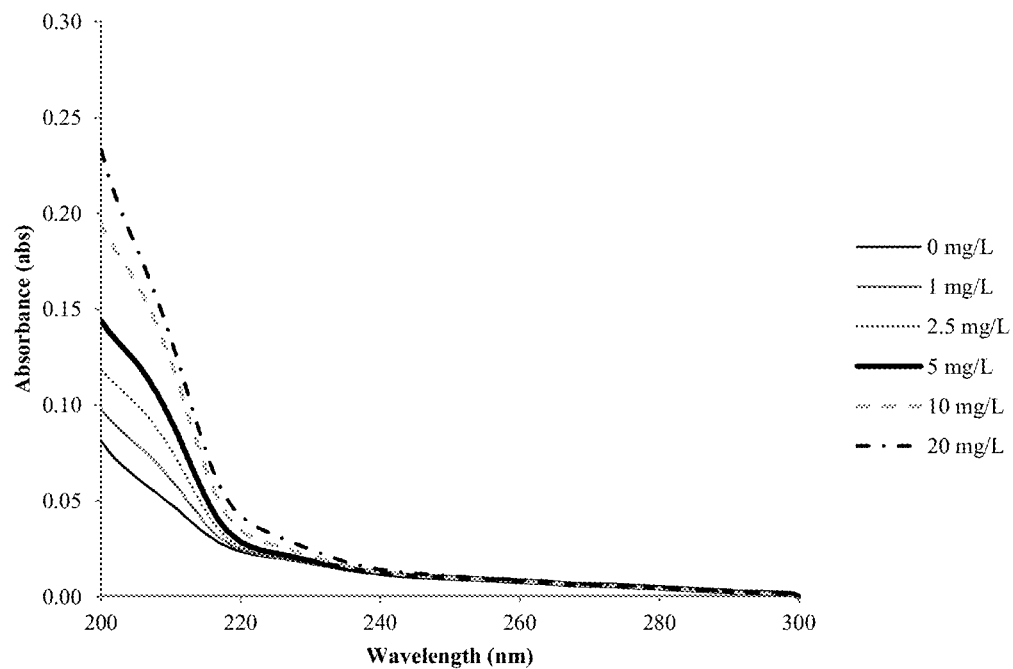
FIG. 1 depicts absorbance scans between 200 nm and 300 nm for various polymers at a range of concentrations between 0 mg/L and 20 mg/L in water: (a) Zetag polymer; (b) SNF 475; (c) SNF 4400; (d) SNF 4600; and (e) SNF 4800.
Figure 1B:
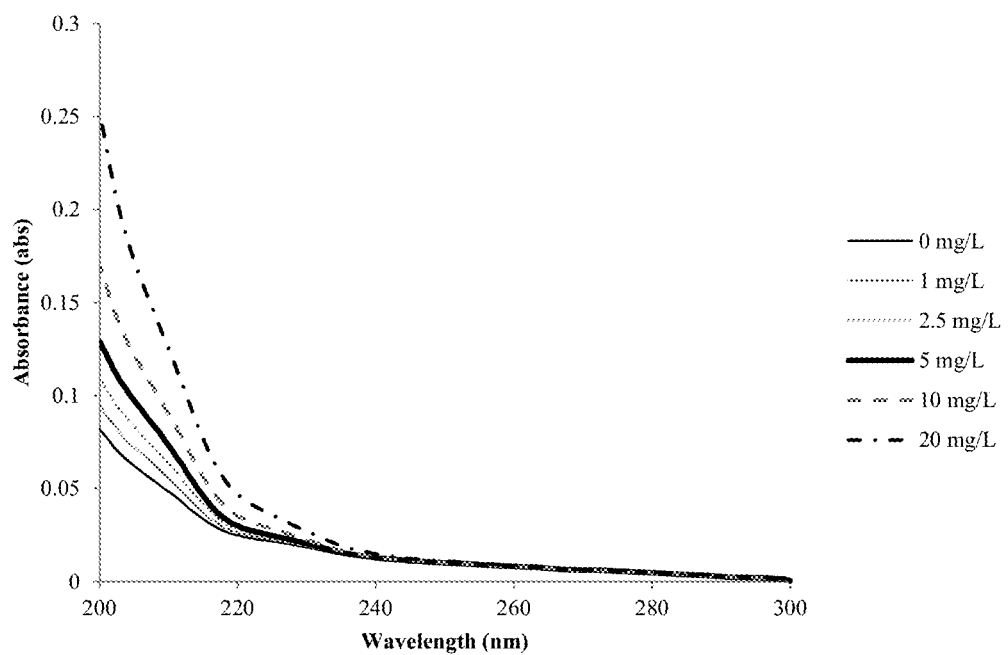
Figure 1C:
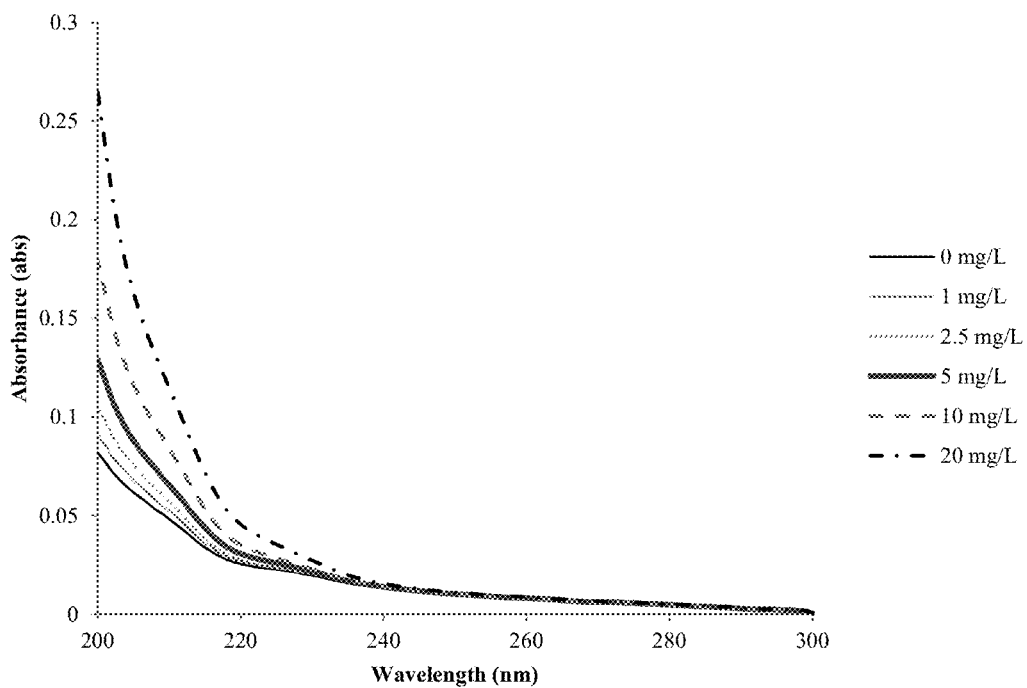
Figure 1D:
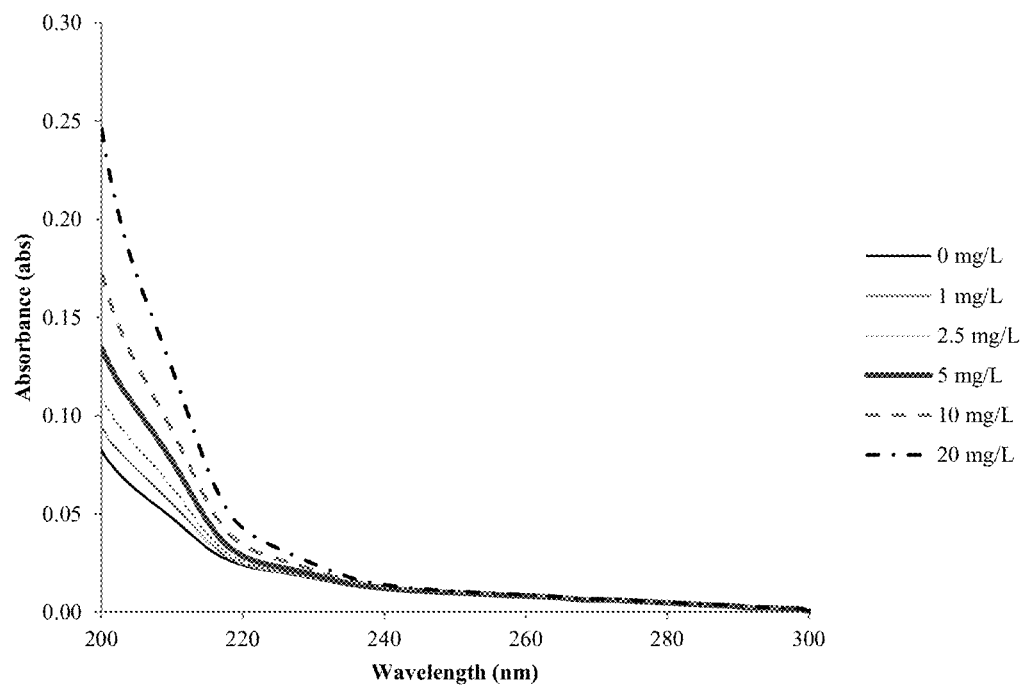
Figure 1E:
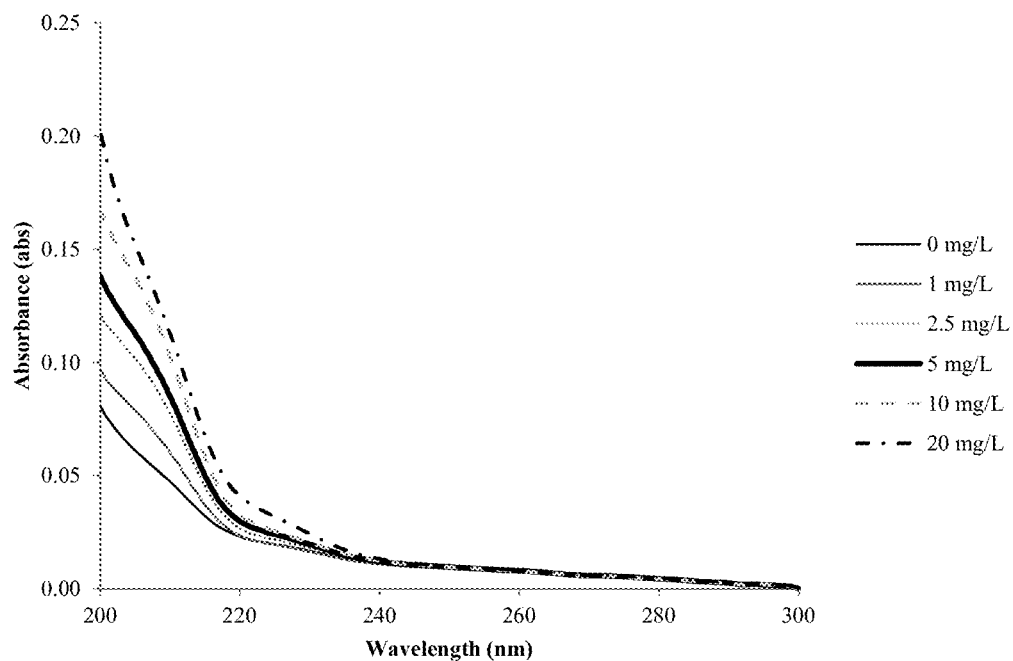
Figure 2A:
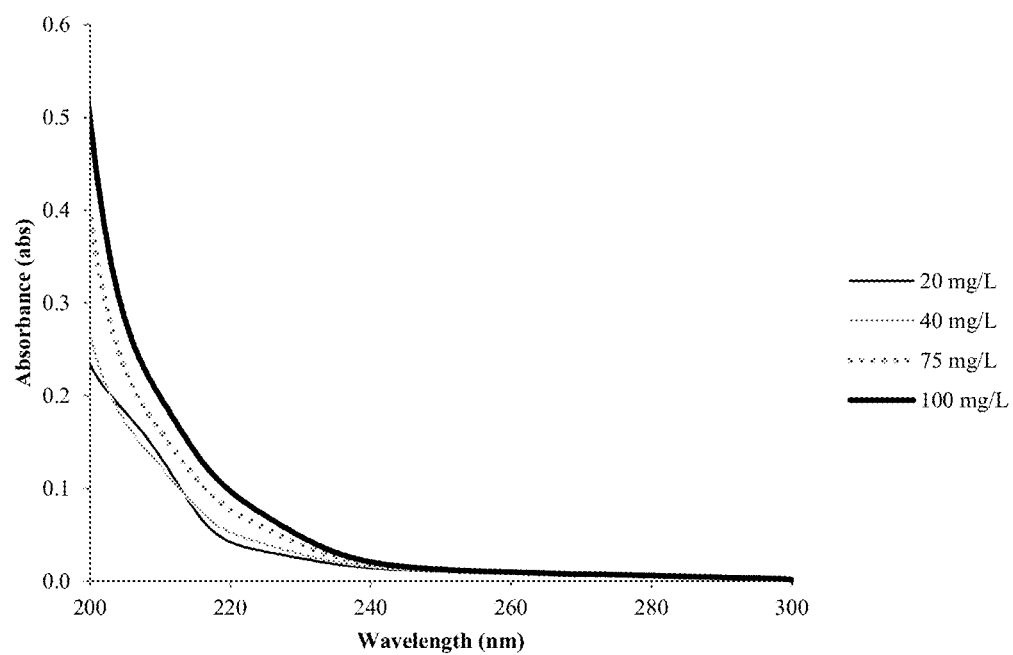
FIG. 2 depicts absorbance scans between 200 nm and 300 nm for various polymers at a range of concentrations between 20 mg/L and 100 mg/L in water: (a) Zetag polymer; (b) SNF 475; (c) SNF 4400; (d) SNF 4600; and (e) SNF 4800.
Figure 2B:
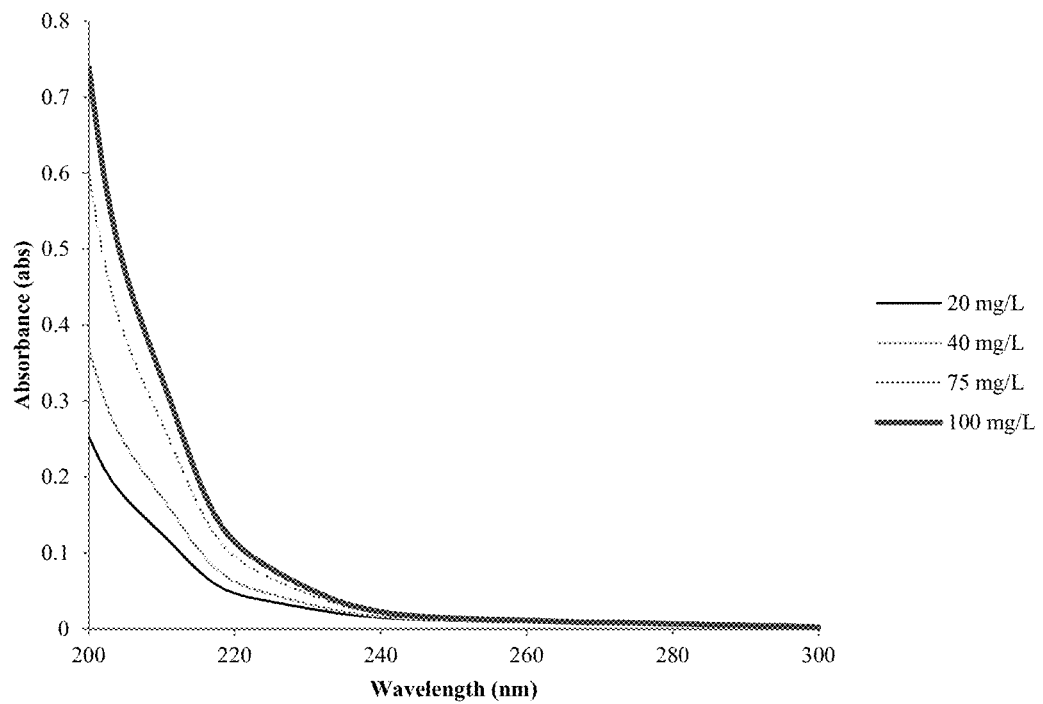
Figure 2C:
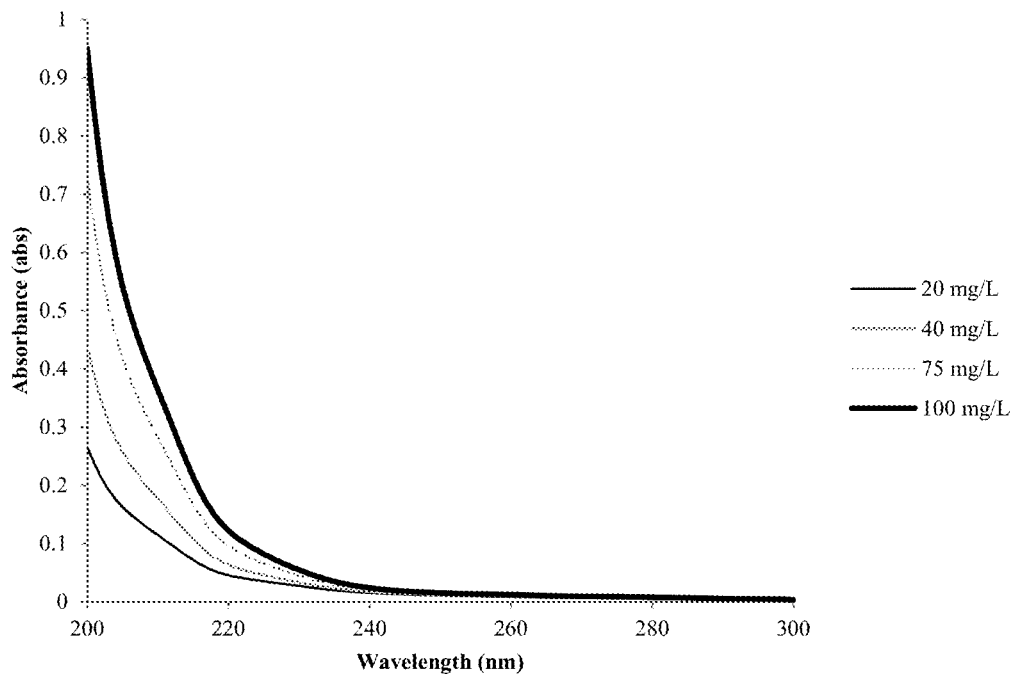
Figure 2D:
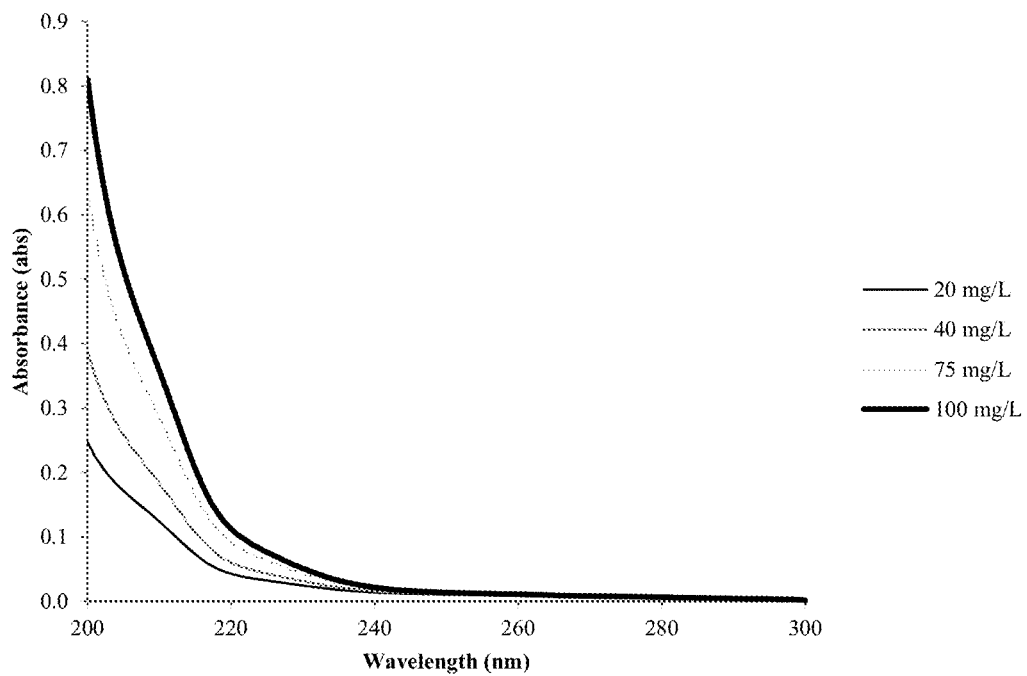
Figure 2E:
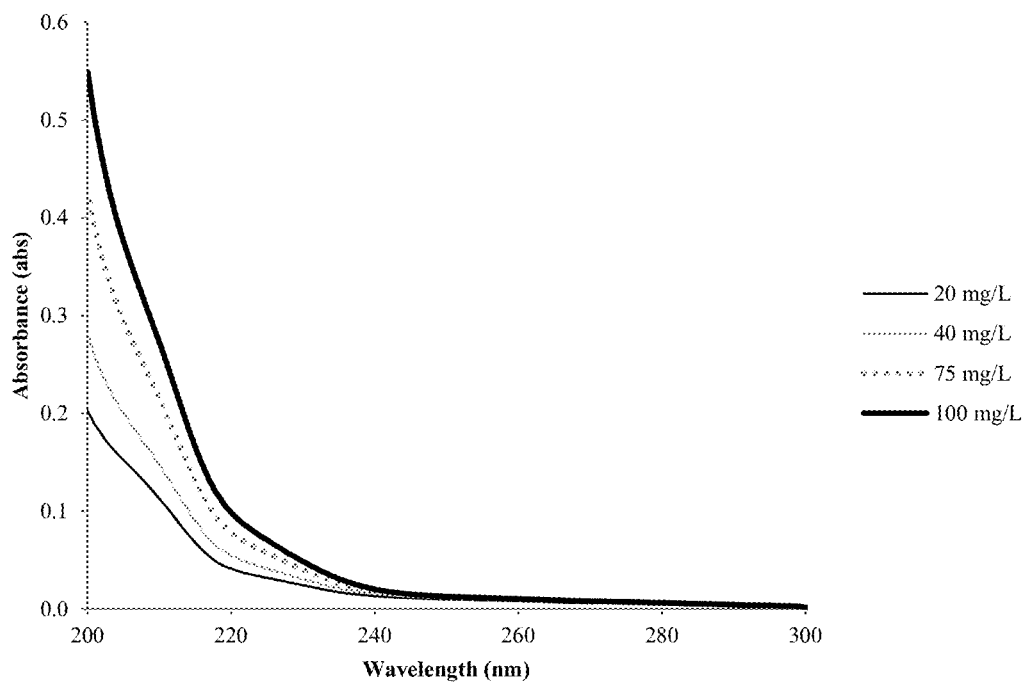
Figure 3A:
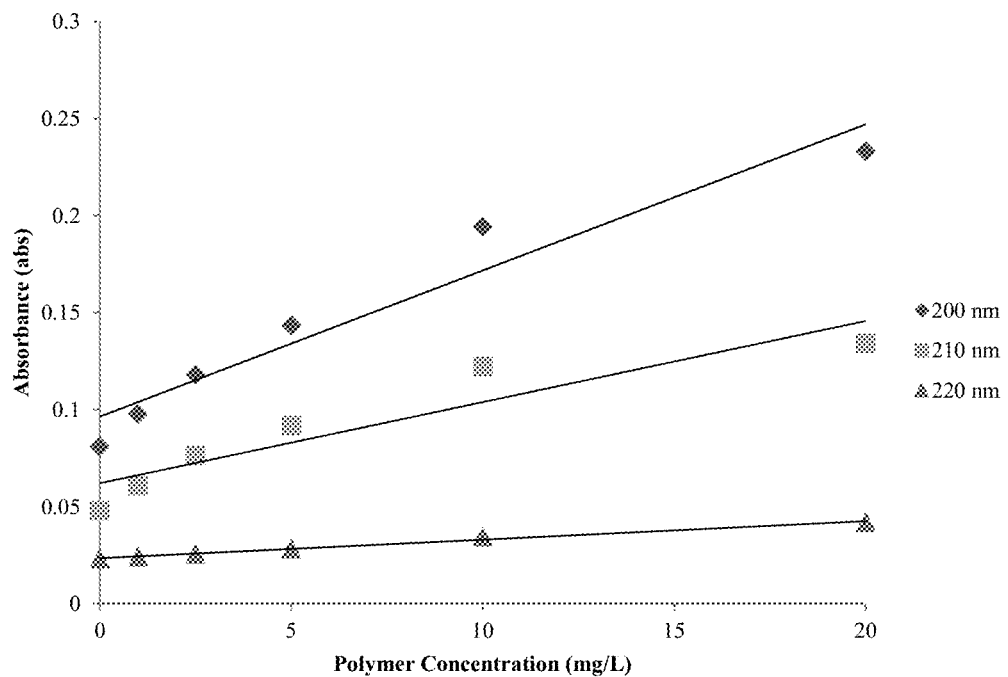
FIG. 3 graphically depicts the relationship between absorbance and polymer concentration for various polymers at 200 nm, 210 nm, and 220 nm at a range of concentrations between 0 mg/L and 20 mg/L in water: (a) Zetag polymer; (b) SNF 475; (c) SNF 4400; (d) SNF 4600; and (e) SNF 4800.
Figure 3B:
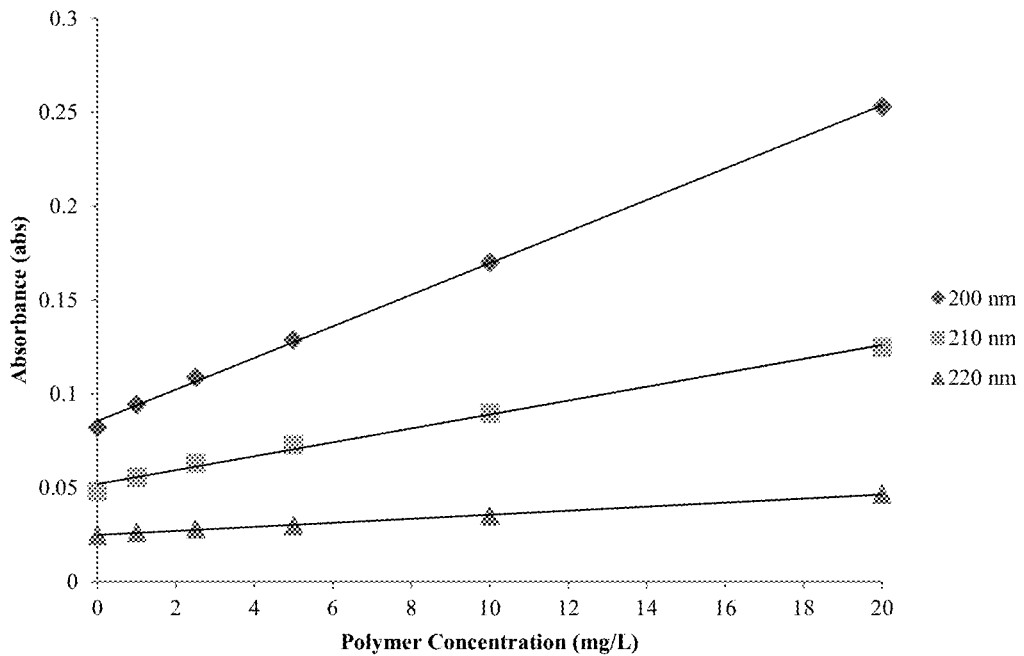
Figure 3C:
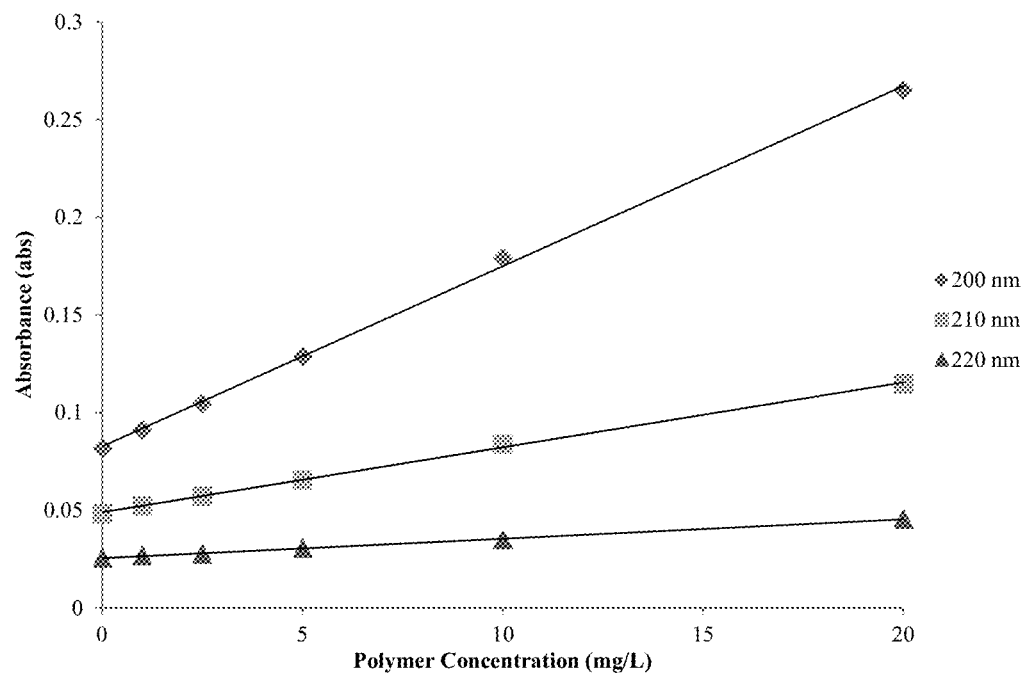
Figure 3D:
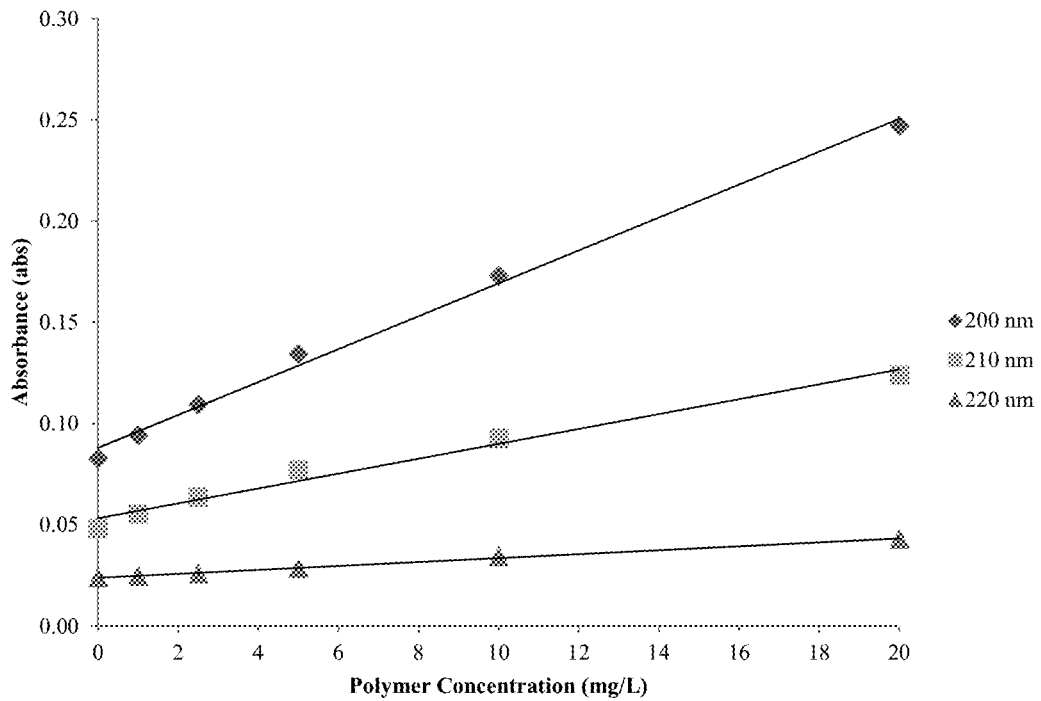
Figure 3E:
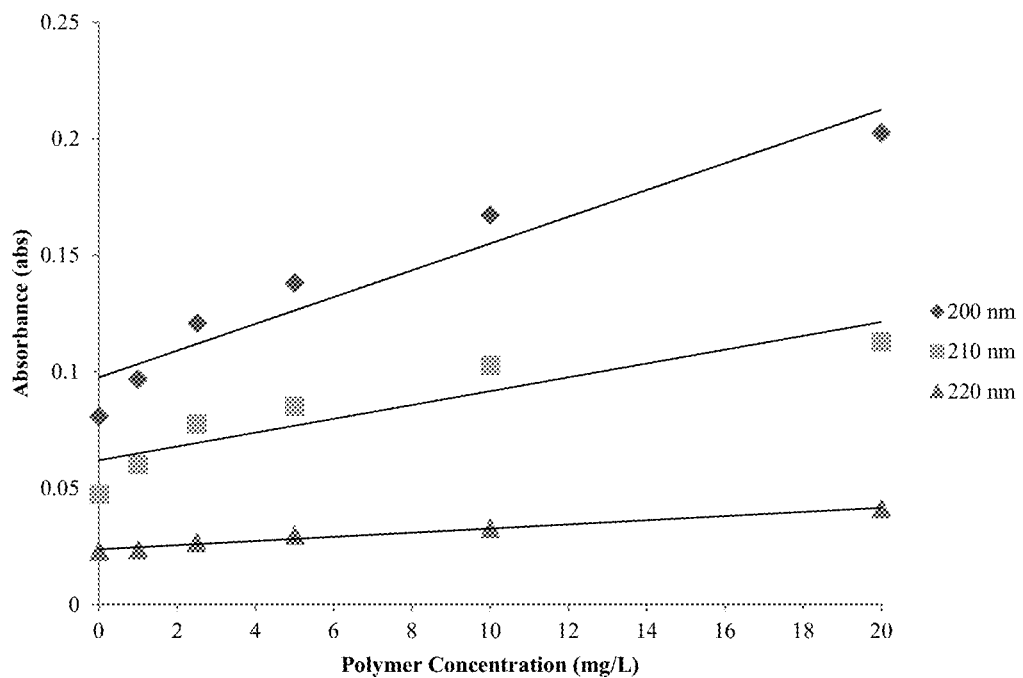
Figure 4A:
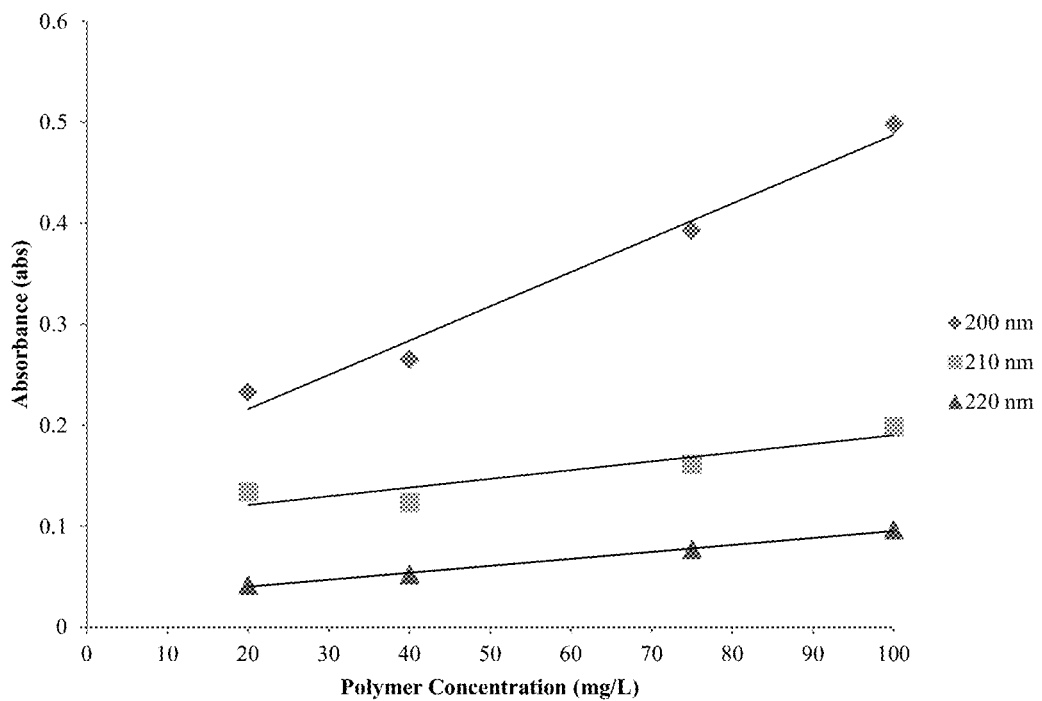
FIG. 4 graphically depicts the relationship between absorbance and polymer concentration for various polymers at 200 nm, 210 nm, and 220 nm at a range of concentrations between 20 mg/L and 100 mg/L in water: (a) Zetag polymer; (b) SNF 475; (c) SNF 4400; (d) SNF 4600; and (e) SNF 4800.
Figure 4B:
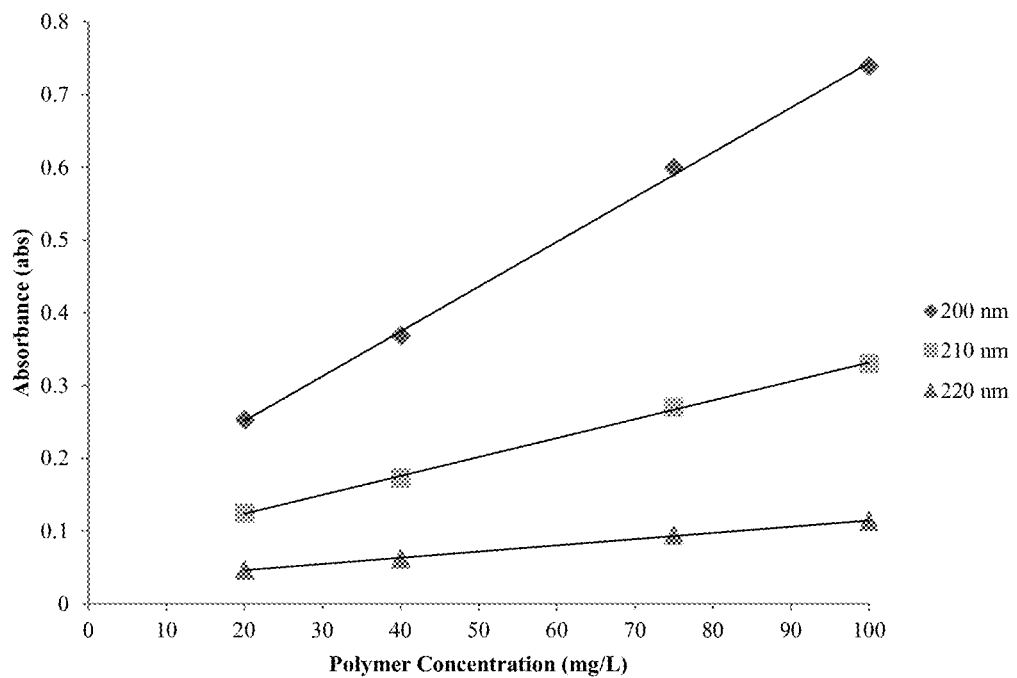
Figure 4C:
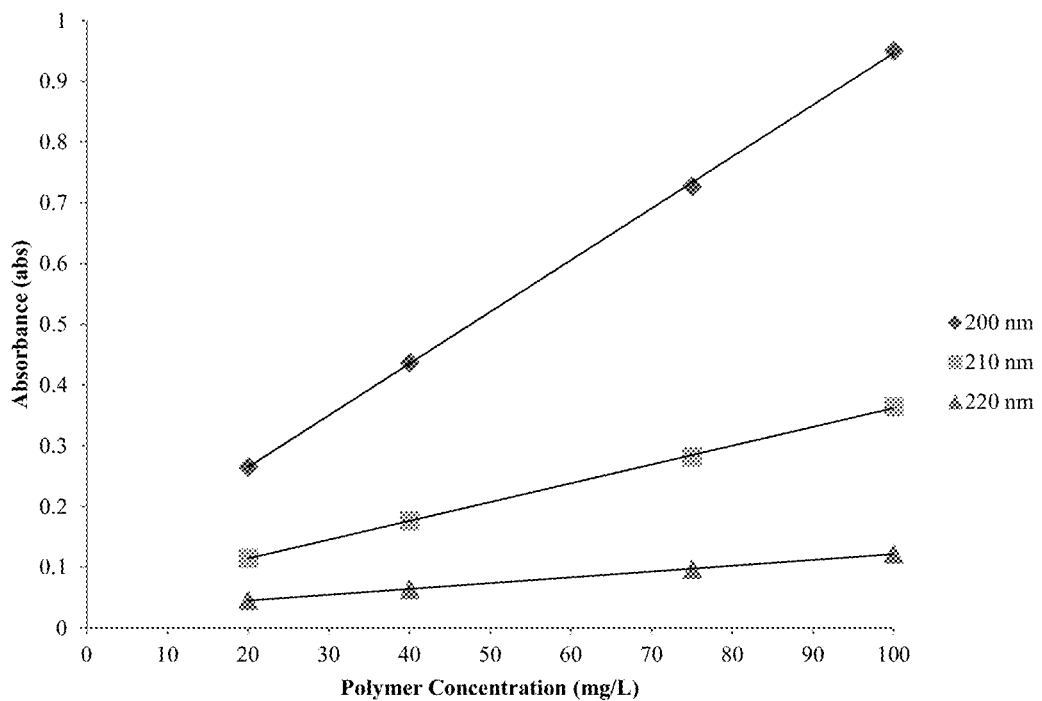
Figure 4D:
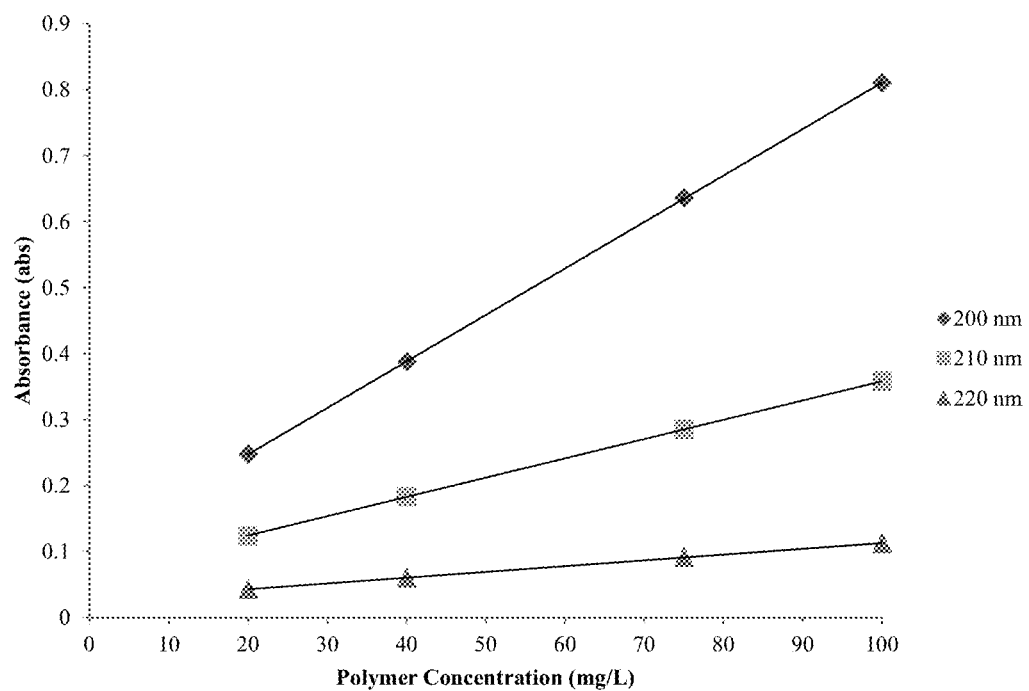
Figure 4E:
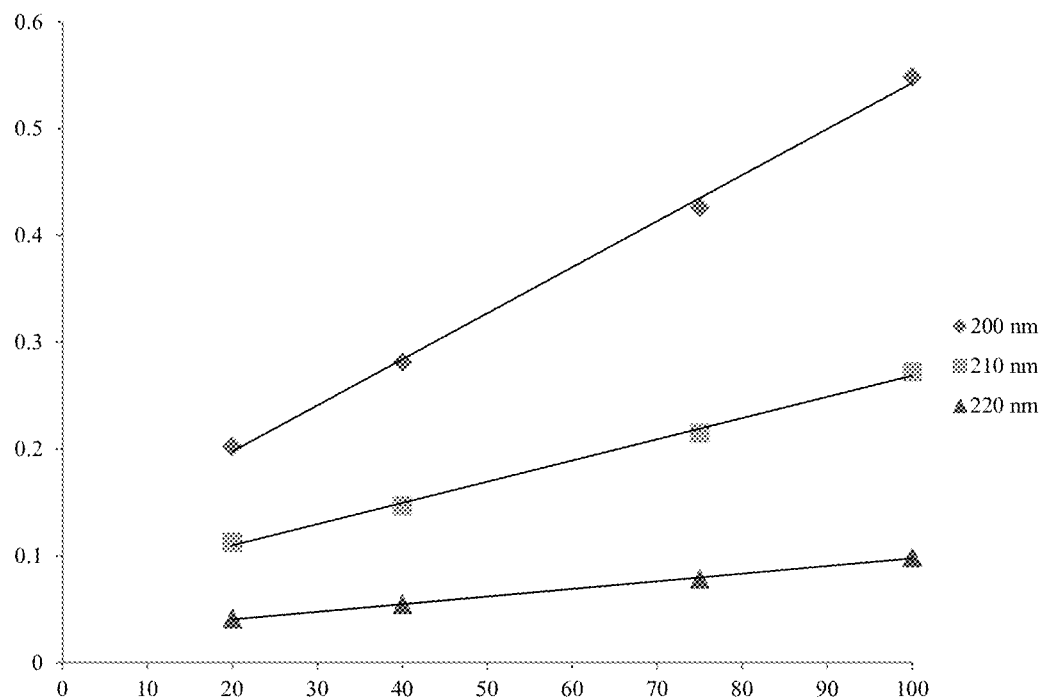

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "process stream" refers to a stream to which a treatment agent, such as a flocculating agent, is added. The term process stream is meant to refer to any stream associated with an industrial or treatment process, and includes side streams, recycle streams, and effluents from such processes. In one embodiment, the process stream is a water-based stream comprising suspended particles. In another embodiment, the process stream originates from an industrial (such as food industry, beverage industry, textiles, manufacturing etc.) or treatment process. Exemplary industrial or treatment processes are those comprising the treatment of: drinking water sources, domestic wastewater, industrial wastewater, contaminated environmental sites, drinking water sludge, domestic wastewater sludge, industrial wastewater sludge, and tailings from gas, oil and mining industries (e.g. from oil sands and the like).

As those of skill in the art will appreciate, the concentration of suspended particles in the process stream varies widely depending on the type of industrial or treatment process from which it originates. For instance, process streams originating from drinking water or domestic wastewater treatment processes typically have a low concentration of suspended particles, whereas process streams originating from treatment processes for tailings from oil sands or from the mining industry typically have a higher concentration of suspended particles.

As used herein, "treatment agent" refers to any agent that is added to a process stream to promote aggregation of solid material for easier handling, separation, or disposal. An exemplary treatment agent is a flocculating agent, such as a polymer or an inorganic conditioner.

As used herein, "flocculating agent" refers to agents that cause the aggregation of certain materials within the process stream into solid aggregates. The aggregates can then be removed in any separation process, for example, in a centrifugation or a filtration process. The method, process, and system of the present application can be used in detecting, quantifying, monitoring and/or adjusting the amount of any flocculating agent, such as, but not limited to, synthetic polymers, biodegradable polymers, and inorganic conditioners.

As used herein, the term "polymer" means a molecule of high relative molecular mass, the structure of which essentially comprises multiple repetition of units derived from molecules of low relative molecular mass. A molecule can be regarded as having a high relative molecular mass if the addition or removal of one or a few of the units has a negligible effect on the molecular properties (see IUPAC Recommendations 1996). In another embodiment, the polymer contains functional groups such as aromatic rings, carbonyl groups, and polyenes.

Exemplary synthetic polymers for use as flocculating agents can be selected from, but are not limited to, an (acrylamide)-(dimethylaminoethyl acrylate) copolymer, an (acrylamide)-(chloromethylated dimethylaminoethyl acrylate) copolymer, a polyaminoalkylmethacrylate or copolymer thereof, a polyacrylesteracrylamide copolymer, a polyamine such as a quaternary polyamine, a polyamidoamine, a polyethyleneimine, a dicyandiamide, a chitosan, a polyacrylamide, a (polyacrylamide)-(carboxylic acid salt) copolymer, a (polyacrylamide)-(sulphonic acid salt) copolymer, a polyethylene oxide, a polyacrylate such as sodium polyacrylate, an (acrylamide)-(sodium acrylate) copolymer, carboxylmethyl cellulose, a (diallyldimethyl ammonium chloride)-(acrylic acid) copolymer, a (diallyldimethyl ammonium chloride)-(acrylamide) copolymer, an (acrylamide)-(acrylic acid)-(chloromethylated dimethylaminoethyl acrylate) copolymer, polydiallyldimethyl ammonium chloride (PolyDADMAC), a sodium polystyrene sulphonate-based polymer, a sodium polyvinylsulphonate-based polymer, an (acrylic acid)-(2-acrylamido-2-methylpropanesulphonic acid) copolymer, or a mixture thereof. In one embodiment, the synthetic polymer is a polyacrylamide, polydiallyldimethyl ammonium chloride, or a polyamine. In another embodiment, the synthetic polymer is a polyacrylamide.

In another embodiment, the synthetic polymer is CIBA Zetag 7587, SNF Flo Polymer CA 475, SNF Flo Polymer CA 4400, SNF Flo Polymer CA 4600, SNF Flo Polymer CA 4800, Hydrex 3572 (Veolia Inc.), FloPolymer CB 4350 (SNF Inc.), CA475, CAB4500, Hydrex 6783 (PolyDADMAC), Hydrex 6704 (polyamine polymer), or combinations thereof.

Exemplary biodegradable polymers include, but are not limited to, starch-based polymers and cellulose-based polymers.

Exemplary inorganic conditioners include, but are not limited to, alum, ferric chloride, ferrous chloride, aluminum perchloride, or lime.

As used herein, the "absorption property" of a sample refers generally to any property used to describe the interaction of light with the sample. Exemplary absorption properties include, but are not limited to, absorbance, transmittance, reflection, and scattering. In one embodiment, the absorption property is selected from absorbance or transmittance.

Methods for Detecting an Amount of Treatment Agent in a Process Stream, and Related Processes The present application is directed to a method, process, and system for detecting an amount of treatment agent in a process stream comprising the step of measuring at least one absorption property of a sample obtained from the process stream. As described in more detail below, this detection method can be incorporated in a method, process, or system for quantifying, monitoring and/or regulating the amount of treatement agent in a process stream.

During treatment of a process stream arising from, for example, one of the above-noted industrial or treatment processes, the process stream can be dewatered or thickened to reduce the volume of liquid waste, or to produce a more solid-like waste for disposal or reuse. The process stream can be separated into a liquid-rich stream and a solid-rich stream. Depending on the source, the solid-rich stream can be converted into fertilizer, or otherwise disposed of The liquid-rich stream can also be referred to as a "centrate" or a "filtrate," depending on the separation technique used, in reference to centrifuges and filters, respectively. In some cases, a treatment agent such as a flocculating agent (e.g. a polymer or an inorganic conditioner) can be added, for example, to promote aggregation of solid material for easier handling, separation, or disposal. The process of adding such agents is termed conditioning.

UV-vis spectrophotometry can be used to identify polymers that contain certain functional groups, including aromatic rings, carbonyl groups, and polyenes (Stuart, 2002). Polymers used in wastewater treatment (i.e., polyacrylamide) typically contain carbonyl groups (Chang et al., 2002), and as such, UV-vis spectrophotometry should be a viable method for detecting polymers, as well as other treatment agents used in wastewater treatment and other industrial or treatment processes.

A new method was developed to measure the polymer concentration in liquids and slurries using UV-vis spectroscopy. A strong linear relationship was observed between the absorbance values and the polymer concentrations at both low and high polymer concentrations in the UV-vis range. This allows the calculation of polymer concentration in an unknown sample by simply measuring its absorbance. Instead of absorbance, other absorbance related properties such as light transmittance or scattering can be used.

The method can be used for liquids such as drinking water, surface water, domestic wastewater and industrial wastewater as well as for slurries such as water and wastewater treatment sludge, industrial sludge, pulp and paper sludge, tailings and other mine waste.

In one embodiment of the present application, there is provided a method of detecting an amount of a treatment agent, such as a flocculating agent, in a process stream comprising the step of measuring at least one absorption property of a sample obtained from the process stream at a wavelength of less than about 250 nm.

In one embodiment, the process stream is a water-based stream comprising suspended particles. In another embodiment, the process stream is from an industrial or treatment process. In yet another embodiment, the industrial or treatment process comprises the treatment of: drinking water sources, domestic wastewater, industrial wastewater, a contaminated environmental site, drinking water sludge, domestic wastewater sludge, industrial wastewater sludge, or tailings from gas, oil and mining industries.

In one embodiment, the flocculating agent is a synthetic polymer. In another embodiment, the synthetic polymer is: an (acrylamide)-(dimethylaminoethyl acrylate) copolymer, an (acrylamide)-(chloromethylated dimethylaminoethyl acrylate) copolymer, a polyaminoalkylmethacrylate or copolymer thereof, a polyacrylesteracrylamide copolymer, a polyamine such as a quaternary polyamine, a polyamidoamine, a polyethyleneimine, a dicyandiamide, a chitosan, a polyacrylamide, a (polyacrylamide)-(carboxylic acid salt)

copolymer, a (polyacrylamide)-(sulphonic acid salt) copolymer, a polyethylene oxide, a polyacrylate such as sodium polyacrylate, an (acrylamide)-(sodium acrylate) copolymer, carboxylmethyl cellulose, a (diallyldimethyl ammonium chloride)-(acrylic acid) copolymer, a (diallyldimethyl ammonium chloride)-(acrylamide) copolymer, an (acrylamide)-(acrylic acid)-(chloromethylated dimethylaminoethyl acrylate) copolymer, polydiallyldimethyl ammonium chloride, a sodium polystyrene sulphonate-based polymer, a sodium polyvinylsulphonate-based polymer, an (acrylic acid)-(2-acrylamido-2-methylpropanesulphonic acid) copolymer, or a mixture thereof. In yet another embodiment, the synthetic polymer is a polyacrylamide.

In another embodiment, the flocculating agent is a biodegradable polymer, such as a starch-based polymer or a cellulose-based polymer. In still another embodiment, the flocculating agent is an inorganic conditioner, such as alum, ferric chloride, ferrous chloride, aluminum perchloride, or lime.

In yet another embodiment, the flocculating agent can comprise one or more polymers and/or one or more inorganic conditioners in combination. Such combinations can be used simultaneously or sequentially in the industrial or treatment processes referenced herein, and the methods, processes, and systems of the present application can be used to monitor, detect, quantify and/or regulate one or all of the agents used in such combinations.

In one embodiment, the at least one absorption property is selected from absorbance and transmittance. In a specific embodiment, the at least one absorption property is absorbance.

In another embodiment, a pretreatment step is implemented to remove or reduce the amount of solid material in the sample prior to measuring the at least one absorption property. Such a pretreatment step may be required to remove or reduce the amount of the particles and solids from liquid and slurry samples before measuring their absorbance in the UV-vis range. This can be achieved with various separation methods including mechanical, physical and chemical methods. In an alternative embodiment, the sample is diluted prior to measuring the at least one absorption property. As those of skill in the art will appreciate, the degree of dilution of samples required for accurate measurement will vary depending on the amount and nature of suspended material in the original samples. Exemplary, and non-limiting, dilution ranges for a typical sludge centrate are from about 1:10 to about 1:150, from about 1:25 to about 1:150, or from about 1:50-1:100. Typically, dilution would be performed using water.

In one embodiment, the treatment agent exhibits an absorbance maximum (or maxima) and/or exhibits high absorbance in the range of from about 150 nm to about 240 nm. In another embodiment, the treatment agent exhibits an absorbance maximum (or maxima) and/or exhibits high absorbance in the range of from about 170 nm to about 240 nm, from about 170 nm to about 220 nm, or from about 190 nm to about 220 nm. In another embodiment, the treatment agent is a flocculating agent, such as a synthetic polymer, a biodegradable polymer, or an inorganic conditioner. In yet another embodiment, the flocculating agent is a polyacrylamide, polydiallyldimethyl ammonium chloride, a polyamine, ferric chloride, ferrous chloride, or alum. In still another embodiment, the flocculating agent exhibits high absorbance at a wavelength of about 190 nm.

Thus, in one embodiment, the wavelength used to obtain a measurement of an absorption property is between about 150 nm and about 240 nm. In another embodiment, the wavelength is between about 170 nm and about 240 nm. In yet another embodiment, the wavelength is between about 170 nm and about 220 nm. In still yet another embodiment, the wavelength is between about 190 nm and about 220 nm. In another embodiment, the wavelength is about 190 nm.

To increase the sensitivity of the method, the absorbance should be measured at wavelengths where samples and treatment agents absorb light strongly. This wavelength could be different when different treatment agents are used.

The concentration of polymer present in samples obtained from process streams treated with same can vary widely according to the application. For instance, for wastewater/sludge applications, the polymer concentration in the filtrate/centrate is generally less than about 100 mg/L, and more typically less than or equal to about 20 mg/L. In applications relating to gas, oil and mining industries, the polymer concentration in the filtrate/centrate can be several hundreds of mg/L, whereas in drinking water applications the polymer concentration can be less than about 1 mg/L.

In one embodiment, the industrial or treatment process comprises the treatment of domestic wastewater, industrial wastewater, domestic wastewater sludge, or industrial wastewater sludge, and the polymer is a synthetic polymer and is present at a concentration of less than about 100 mg/mL in the process stream. In another embodiment, the polymer is present at a concentration of less than or equal to about 20 mg/mL in the process stream.

In another embodiment of the present application, there is provided a process for regulating an amount of a treatment agent added to a process stream comprising:
  (i) measuring at least one absorption property of a sample obtained from the process stream at a wavelength of less than about 250 nm;
  (ii) comparing the measured at least one absorption property to a preselected value that corresponds with a desired concentration of the treatment agent; and
  (iii)(a) adjusting the amount of treatment agent added to the process stream if the measured at least one absorption property is outside a predetermined range around the preselected value, and
    (b) repeating steps (i), (ii) and (iii)(a) until the measured at least one absorption property of the sample is within a predetermined range around the preselected value, and thereafter maintaining the amount of treatment agent added to the process stream; or
  (iv) maintaining the amount of treatment agent added to the process stream if the measured at least one absorption property is within a predetermined range around the preselected value.

In another embodiment, steps (i), (ii), and (iii) or (iv) are repeated at predetermined intervals during the industrial or treatment process. Such predetermined intervals can be readily determined by those of skill in the art.

In another embodiment, the treatment agent is a flocculating agent as described above. In another embodiment, the process stream is as described above.

In another embodiment, the at least one absorption property is selected from absorbance and transmittance.

In another embodiment, the at least one absorption property is absorbance. In yet another embodiment, the preselected value is determined by a method comprising:
  adding the treatment agent to a test process stream in a range of amounts;
  obtaining a test sample from the test process stream following addition of each amount of the treatment agent, and measuring the absorbance of each test sample at a wavelength of less than about 250 nm; and plotting the absorbance for each test sample versus the amount of treatment agent added to the test process stream, the plot forming a generally U-shaped or V-shaped curve, and the preselected value corresponding to an absorbance value at or near a minimum in the plot.

In still another embodiment, the at least one absorption property is transmittance.

In yet another embodiment, the preselected value is determined by a method comprising:

adding the treatment agent to a test process stream in a range of amounts;

obtaining a test sample from the test process stream following addition of each amount of the treatment agent, and measuring the transmittance of each test sample at a wavelength of less than about 250 nm; and plotting the transmittance for each test sample versus the amount of treatment agent added to the test process stream, the plot forming a generally inverted U-shaped or V-shaped curve, and the preselected value corresponding to a transmittance value at or near a maximum in the plot.

Absorbance values at or near a minimum in the plot can be values that are within, for example, about 25% of the minimum absorbance value in the plot. Transmittance values at or near a maximum in the plot can be values that are within, for example, about 25% of the maximum transmittance value in the plot.

In another embodiment, the wavelength is as described above. In another embodiment, the process further comprises a pretreatment step to remove solid material from the sample prior to measuring the at least one absorption property. In another embodiment, the process further comprises a pretreatment step to remove solid material from each of the test samples prior to measuring the at least one absorption property of each of the test samples. In still another embodiment, the process further comprises diluting the sample prior to measuring the at least one absorption property. In yet another embodiment, the process further comprises diluting each of the test samples prior to measuring the at least one absorption property of each of the test samples.

As those of skill in the art will appreciate, the period of time between additions of the treatment agent will vary according to the application (e.g. sludge characteristics). As well, the amount of treatment agent (such as a flocculating agent) added to a process stream will vary according to the application and can readily be determined by those of skill in the art. For instance, the amount of treatment agent can be determined according to the weight of solids recovered from the industrial or treatment process.

If the measured at least one absorption property of the sample at the relevant wavelength is within a predetermined range around the preselected value, the amount of treatment agent that is added to the process stream is maintained. If the measured at least one absorption property of the sample at the relevant wavelength is outside the predetermined range around the preselected value, the amount of treatment agent that is added to the process stream is adjusted. It will be understood by those of skill in the art that the predetermined range of values for the at least one absorption property around the preselected value will vary according to the application; for instance, the predetermined range for treatment of drinking water sources would perhaps be narrower than the predetermined range for treatment of industrial wastewater. Plant operators can readily identify a desired concentration of flocculating agent, as well as select appropriate ranges around the preselected value of the at least one absorption property, according to plant operating requirements. For instance, the predetermined range for the at least one absorption property of the sample can be defined as being within a certain percentage of the preselected value. In some embodiments, the predetermined range can be defined as being, for example, within about 75%, 70%, 65%, 60%, 55%, 50%, 45%, 40%, 35%, 30%, 25%, 20%, 15%, 10%, or 5% of the preselected value. In other embodiments, the predetermined range can be defined as being within about 20%, 19%, 18%, 17%, 16%, 15%, 14%, 13%, 12%, 11%, 10%, 9%, 8%, 7%, 6%, 5%, 4%, 3%, 2%, or 1% of the preselected value.

The preselected value of the at least one absorption property of a sample obtained from the process stream measured at a wavelength of less than about 250 nm corresponds with a desired concentration of the treatment agent in the process stream. The desired concentration of the treatment agent, such as a synthetic polymer, can be based on legal limits according to the application, and/or can be based on other factors, such as, for example, an optimum concentration of the treatment agent that achieves maximization of cake solids, and/or maximization of filtrate and centrate quality. The preselected value of the at least one absorption property of a sample obtained from the process stream can therefore be an optimal value corresponding with the optimum concentration of the treatment agent in the process stream. As would be readily appreciated by a worker skilled in the art, the optimum concentration of the treatment agent can be the absolute optimum value (i.e., the value that would produce the highest quality filtrate and centrate quality), or it can be a value that is sufficient to obtain filtrate and centrate of a quality that is sufficient to meet the requirements of a particular process. For example, the quality requirements of a drinking water process will be significantly different from the requirements of a waste water treatment process where the output is to be discarded or used in a downstream application with less stringent requirements than drinking water.

Thus, in addition to measuring the polymer concentration in samples, the method is also useful in determining the optimum polymer dose required during conditioning. When the optimal polymer dose is exceeded, an increase in the polymer concentration would be observed in the liquid stream exiting a separation process.

For instance, Example 3 below relates to optimization of polymer dose in a sludge dewatering process. In this Example, the preselected value for the sample absorbance corresponding to a desired concentration of polymer is selected based on the minimum in a plot of absorbance (at 191.5 nm) versus polymer dose (see FIGS. 17 and 18), which produces a generally U-shaped or V-shaped curve. Results of dewatering tests (capillary suction time (CST) and filtrate volume) are also depicted on the Y axis in FIGS. 17 and 18, and from these plots it can be determined that the preselected (optimal) value for the sample absorbance corresponds to the highest filtrate volume and lowest capillary suction time (CST).

Figure 17:
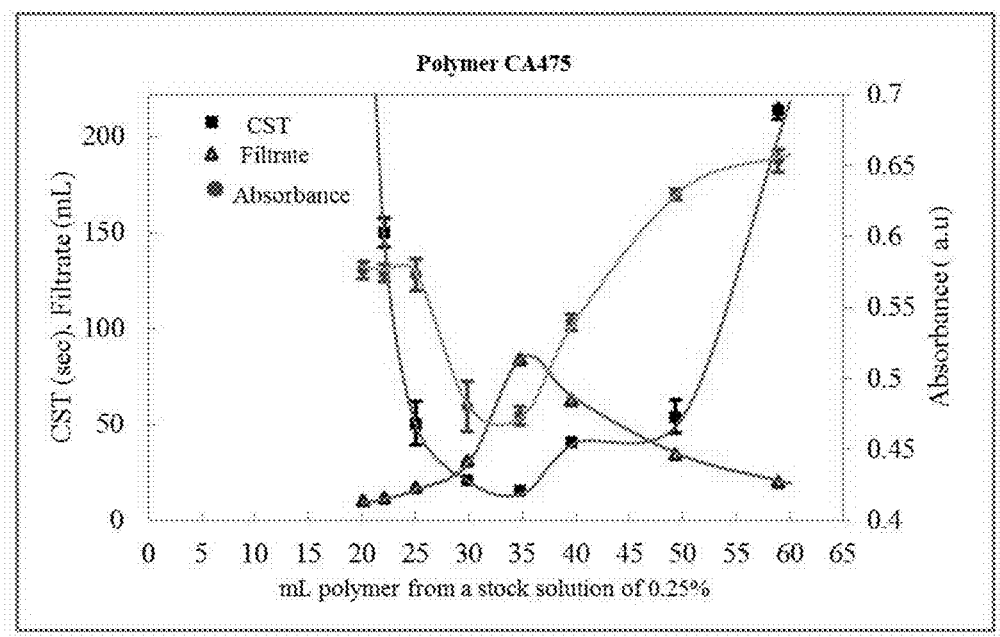
FIG. 17 graphically depicts a plot of capillary suction time (CST)/filtrate volume and absorbance versus polymer dose for sludge samples from a wastewater treatment plant treated with polymer CA475.
Figure 18:
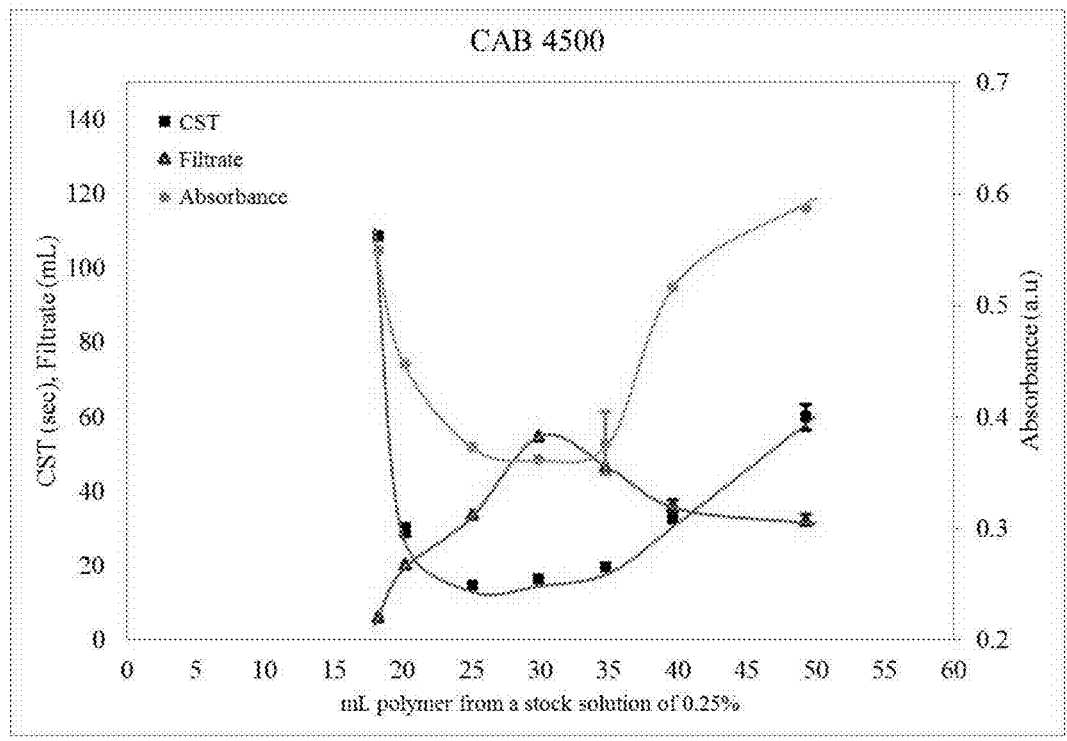
FIG. 18 graphically depicts a plot of capillary suction time (CST)/filtrate volume and absorbance versus polymer dose for sludge samples from a wastewater treatment plant treated with polymer CAB4500.

Referring to FIGS. 17 and 18, when the sample absorbance exceeds the preselected value it may fall on either side of the minimum in the generally U-shaped or V-shaped curve. If the sample absorbance falls outside of the predetermined range around the preselected value, it would then be necessary to either increase or decrease the polymer dose in order to bring the absorbance of a sample obtained from the process stream within the predetermined range around the preselected value. Such adjustments can be made incrementally until the measured at least one absorption property of the sample at the relevant wavelength is within the predetermined range around the preselected value. Further, by, for example, using an appropriate algorithm, such as a minimum or maximum search algorithm, in-line monitoring and automatic control of optimum polymer dose can be performed in a continuous or semi continuous manner. Notably, the searching principles can be automated by the use of minimum or maximum searching algorithms that would be incorporated in the controllers described herein. This is discussed in further detail in the following section.

In yet another embodiment of the present application, there is provided a process for monitoring an amount of a treatment agent added to a process stream comprising:
  (i) measuring at least one absorption property of a monitoring sample obtained from the process stream at a wavelength of less than about 250 nm;
  (ii) comparing the measured at least one absorption property to a preselected value that corresponds with a desired concentration of the treatment agent; and
  (iii) generating a signal if the measured at least one absorption property is outside a predetermined range around the preselected value.

In one embodiment, the process further comprises the step of:
  (iv) adjusting the amount of polymer added to the process stream if the measured at least one absorption property is outside the predetermined range around the preselected value.

In yet another embodiment, the process further comprises the step of:
  (v) measuring at least one absorption property of an additional monitoring sample obtained from the process stream at a wavelength of less than about 250 nm;
  (vi) comparing the measured at least one absorption property of step (v) to the preselected value; and
  (vii) maintaining the signal if the measured at least one absorption property of step (v) is outside the predetermined range around the preselected value;
    repeating steps (iv), (v), (vi) and (vii) until the measured at least one absorption property is within the predetermined range around the preselected value; and
    ceasing the signal if the measured at least one absorption property is within the predetermined range around the preselected value; or
  (viii) ceasing the signal if the measured at least one absorption property is within the predetermined range around the preselected value.

In still another embodiment, the adjusting comprises lowering the amount of polymer added to the process stream.

In yet another embodiment, the step of generating the signal comprises activating an alarm.

In another embodiment, the step of ceasing the signal comprises deactivating the alarm.

In another embodiment, the process stream is as described above.

In another embodiment, the treatment agent is a flocculating agent as described above.

In another embodiment, the at least one absorption property is selected from absorbance and transmittance. In yet another embodiment, the at least one absorption property is absorbance.

In another embodiment, the wavelength is as described above.

In still another embodiment, the process further comprises a pretreatment step to remove solid material from the monitoring sample(s) prior to measuring the at least one absorption property. In another embodiment, the process further comprises diluting the monitoring sample(s) prior to measuring the at least one absorption property.

In the studies outlined in Examples 1, 2, and 3, polyacrylamide-based synthetic polymers were used. The method can also be used to measure the concentrations of other organic and inorganic conditioners, flocculation agents, and other treatment agents. Example 4 illustrates the use of the method with non-polyacrylamide synthetic polymers, as well as inorganic conditioners.

Systems for Adding Treatment Agents to Process Streams

In-line UV-vis spectrometers or similar sensors are available in the market and have the capability to generate real-time or near real-time absorbance data. Based on the polymer measurement method invented in this study, a manually operated or a partially or fully automated polymer dose and dewatering optimization system can be developed as illustrated in the Figures.

In one embodiment, of the present application, there is provided a system for regulating or optimizing an amount of a treatment agent added to a process stream, the system comprising means for performing the above-described processes. In one embodiment, the means comprises a spectrophotometer configured to measure the at least one absorption property. In yet another embodiment, the process stream is from an industrial or treatment process, and the spectrophotometer is positioned to measure the at least one absorption property in-line with the industrial or treatment process.

In still yet another embodiment of the present application, there is provided a system for adding a treatment agent to a process stream comprising:
  a treatment agent source for supplying an amount of a treatment agent to the process stream;
  a sensor for measuring at least one absorption property of a sample obtained from the process stream at a wavelength of less than about 250 nm; and
  a controller in communication with the sensor and the treatment agent source, wherein the controller:
    compares the measured at least one absorption property to a preselected value that corresponds with a desired concentration of the treatment agent;
    determines whether or not the amount of the treatment agent supplied to the process stream should be adjusted; and
    adjusts the amount of the treatment agent supplied to the process stream if the measured at least one absorption property is outside a predetermined range around the preselected value, or
    maintains the amount of treatment agent supplied to the process stream if the measured at least one absorption property is within a predetermined range around the preselected value.

In another embodiment, the controller uses a minimum or maximum search algorithm in determining whether or not the amount of treatment agent should be adjusted.

In still yet another embodiment of the present application, there is provided a system for monitoring an amount of a treatment agent added to a process stream comprising:
  a sensor for measuring at least one absorption property of a sample obtained from the process stream at a wavelength of less than about 250 nm;
  means for comparing the measured at least one absorption property to a preselected value that corresponds with a desired concentration of the treatment agent; and means for generating a signal if the measured at least one absorption property is outside a predetermined range around the preselected value.

In another embodiment, the system further comprises means for adjusting the amount of polymer added to the process stream if the measured at least one absorption property is outside the predetermined range around the preselected value. In another embodiment, the adjusting comprises lowering the amount of polymer added to the process stream.

In yet another embodiment, the system further comprises means for ceasing the signal if the measured at least one absorption property is within the predetermined range around the preselected value. In still another embodiment, the means for generating the signal comprises activation of an alarm. In yet another embodiment, the means for ceasing the signal comprises deactivation of the alarm.

In another embodiment, the process stream is as described above.

In another embodiment, the treatment agent is a flocculating agent as described above.

In another embodiment, the at least one absorption property is selected from absorbance and transmittance. In yet another embodiment, the at least one absorption property is absorbance.

In another embodiment, the wavelength is as described above.

In another embodiment, the system further comprises means for pretreating the sample to remove solid material from the sample prior to measuring the at least one absorption property. In still yet another embodiment, the system further comprises means for diluting the sample prior to measuring the at least one absorption property.

In another embodiment, the sensor comprises a spectrophotometer. In still yet another embodiment, the process stream is from an industrial or treatment process, and the spectrophotometer is positioned to measure the at least one absorption property in-line with the industrial or treatment process.

Figure 9:
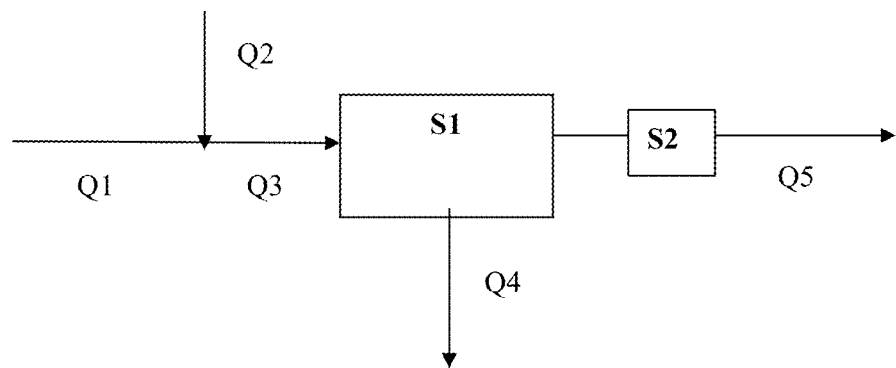
FIG. 9 depicts a system in accordance with one or more embodiments of the present application showing a sensor connected to the liquid-rich stream.
Figure 10:
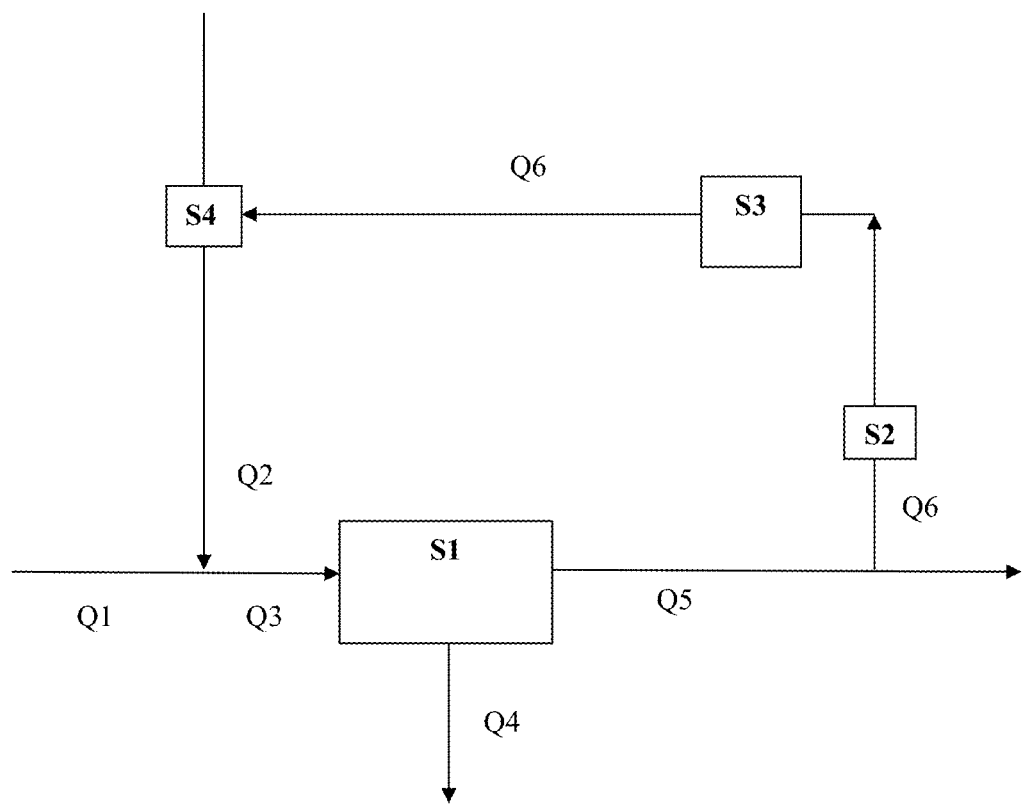
FIG. 10 depicts a system in accordance with one or more embodiments of the present application showing a sensor, a controller, and a flow control device connected to the liquid-rich stream.
Figure 11:
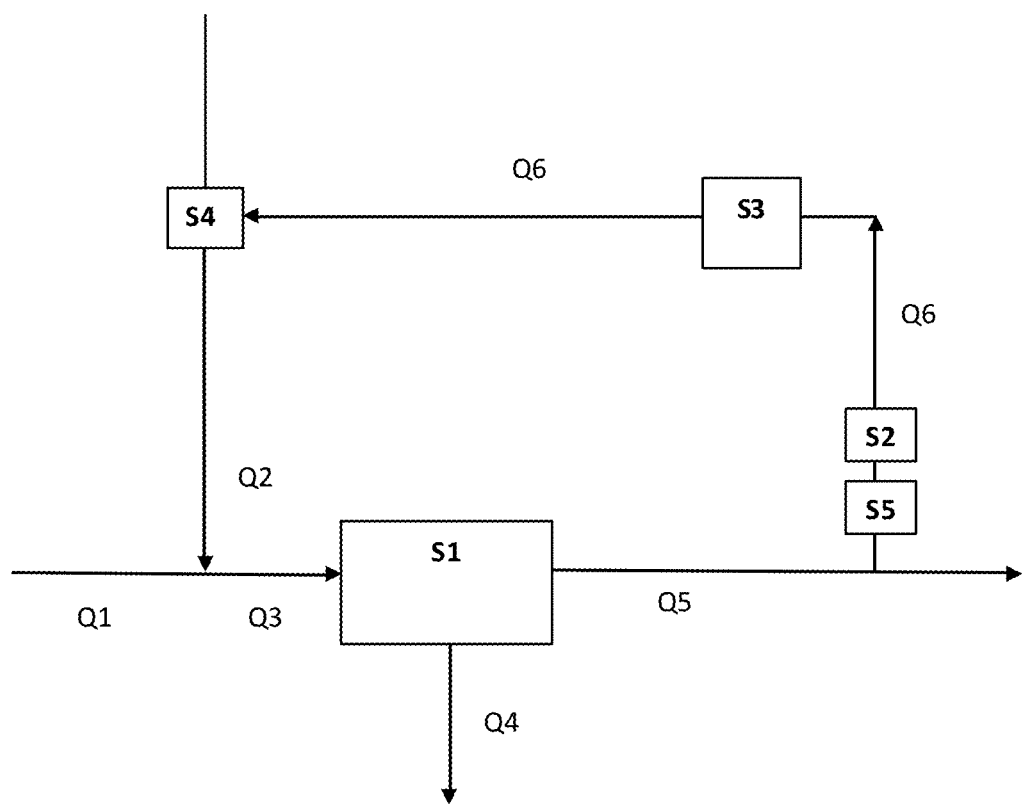
FIG. 11 depicts a system in accordance with one or more embodiments of the present application showing a separation device, a sensor, a controller, and a flow control device connected to the liquid-rich stream.

Exemplary, and non-limiting, systems of the present application are illustrated in FIGS. 9 to 11.

Referring to FIG. 9, Q1 is a liquid or slurry stream, Q2 is a treatment agent stream or liquid or slurry stream carrying the treatment agent, and Q3 is the liquid or slurry stream mixed with the treatment agent. The system includes a separation device designated S1 which separates the incoming stream to liquid-rich (Q5) and solid-rich (Q4) streams. The sensor S2 connected to the liquid-rich stream produces a response based on measured absorbance or a related value.

An alternative embodiment of the present application is illustrated in FIG. 10, wherein Q1 is a liquid or slurry stream, Q2 is a treatment agent stream or liquid or slurry stream carrying the treatment agent, and Q3 is a liquid or slurry stream mixed with the treatment agent. S1 denotes a separation device which separates the incoming stream to liquid-rich (Q5) and solid-rich (Q4) streams. S2 is a sensor connected to the liquid-rich stream Q6 that produces a response based on measured absorbance or a related value. Based on the measured absorbance or related value of the liquid-rich stream, S2 produces a signal which is transmitted to controller S3. Controller S3 using, for example, a preprogrammed algorithm determines an appropriate response for flow control device S4 to control the entering flow of the treatment agent. Flow control device S4 responds to the signal from S3 and controls or regulates the flow of treatment agent entering to flow Q3.

In accordance with one or more embodiments of the present application, device S1 is capable of separating a process stream into two or more streams, such as a liquid-rich stream and a solid-rich stream, and can be a vacuum filter, a filter press, a centrifugal separator, a belt press-type filter, a screw press, or the like. The separation device can treat the entering fluid to produce a liquid-rich stream, which can contain, for example, less than about 0.5% solids, or, in some cases, less than about 0.1% solids. The liquid-rich stream can also be further processed in downstream unit operations. For example, the liquid-rich stream can be further purified, recycled for further treatment, discharged to the environment, or otherwise disposed of. As noted above, the liquid-rich stream is also referred to as a "centrate" or a "filtrate," in reference to centrifuges and filters, respectively; these terms can be used interchangeably.

The materials in the solid-rich ("cake") stream can undergo further processing, be discharged, or otherwise disposed. For example, biosolids can ultimately be converted into fertilizer, or stored for disposal in a landfill. A solid-rich stream can also contain residual amounts of liquid. The dewatered or thickened stream can contain any concentration of solids. For example, the dewatered or thickened stream can contain greater than about 5% solids, greater than about 15% solids, or between about 18 and about 25% solids. In certain embodiments, the stream can contain between about 5% to about 7% solids, between about 40% and about 50% solids, or between about 20% and about 60% solids. Other solid concentrations are also possible.

In the systems described herein, controller S3 can be any system or mechanism that can detect and/or receive the incoming signal from sensor S2, determine and/or generate an appropriate response for flow control device S4, and transmit a signal directing flow control device S4 to give the appropriate response. Controller S3 can be, for example, a mechanical controller, a pneumatic controller, a computer, a semiconductor chip, or the like. Controller S3 can be incorporated into a feedback or a feedforward control loop. In some embodiments, the controller can comprise an algorithm that can arrange the characteristics of one or more streams in a treatment system to process and/or determine an optimal flowrate of treatment agent into Q2. The algorithm can be any algorithm suitable for determining an appropriate response for flow control device S4 and can include routines or techniques such as Minimum or Maximum Search Routines, fuzzy logic techniques, or any algorithms that can determine an optimum based on historical data or trends thereof. Controller S3 can be a "hard-wired" system, or the controller can be programmable and adaptable as needed. The algorithm can be a predetermined algorithm or it can be an algorithm that may adapt with changing process conditions, such as in a process where the flow is pulsatile or randomly distributed.

In the systems described herein, flow control device S4 can be any device that can regulate the flow of treatment agent into Q2. For example, flow control device S4 can be a valve or a pump. In one embodiment, as an example, the throughput rate of a pump that can be a part of flow control device S4 can be altered in response to a signal from controller S3. In another embodiment, the pump can be activated or deactivated in response to a signal from controller S3. In still other embodiments, a valve can be part of flow control device S4 and can be used to regulate the flow of treatment agent. For example, the valve can be a plug cock valve, a gate valve, a diaphragm valve, a globe valve, a butterfly valve, or the like and, in response to signals from controller S3, the valve can respond by fully opening and closing in some embodiments, or by partially opening and closing. Other methods for regulating the flow of treatment agent into treatment agent stream Q2 can also be envisioned. For example, a concentration of treatment agent in stream Q2 can be controlled by the appropriate addition of a diluent to the treatment agent stream.

In one embodiment of the system illustrated in FIG. 10, the system is used for polymer dose and dewatering optimization. Controller S3 using a preprogrammed algorithm (for example a minimum search algorithm if absorbance is used) determines an appropriate response for device S4 to control the entering flow of the flocculating agent. Potential applications for these embodiments of the system of FIG. 10 include, but are not limited to, treatment processes for:

1) Drinking water sludge: In this application, Q1 is sludge generated from drinking water treatment. S1 is a mechanical separation device (such as a centrifuge, belt press filter etc.) or a thickener or settling tank for sludge. Q2 comprises a flocculating agent. Q4 corresponds to collected solids or sludge, and Q5 is effluent water. S2 comprises an in-line UV-vis spectrophotometer. The remainder of the components are as defined above.

For embodiments (2) to (5), components not specifically described are similar to those outlined for (1) above.

2) Domestic wastewater (sewage) sludge: In this application, Q1 is sludge generated from domestic wastewater treatment. S1 is a mechanical separation device (such as a centrifuge, belt press filter etc.) or a thickener, a settling tank or a flotation tank.

3) Industrial wastewater sludge: In this application, Q1 is sludge generated from domestic wastewater treatment. S1 is a mechanical separation device (such as a centrifuge, belt press filter etc.) or a thickener, a settling tank or a flotation tank.

4) Industrial slurries: In this application, Q1 is slurries coming from industrial waste streams. S1 is a mechanical separation device (such as a centrifuge, belt press filter etc.) or a thickener, a settling tank or a flotation tank.

5) Tailings from gas, oil, and mining industries: In this application, Q1 is tailings generated from gas, oil, and mining industries. S1 is a gravity thickener, a reservoir, or a mechanical separation device.

In another embodiment, the system illustrated in FIG. 10 can be used for detecting and regulating the polymer dose. In another embodiment, component S3 is optional. In another embodiment, S3 is present and determines an appropriate response for device S4 to control the entering flow of a treatment agent, such as a flocculating agent. In another embodiment, the system monitors and regulates the polymer dose based on a preset value. In yet another embodiment, component S3 is omitted and the system can be used simply for monitoring polymer concentration. Potential applications for these embodiments of the system of FIG. 10 include, but are not limited to, treatment processes for:

1) Drinking Water: In this application, Q1 can be raw/untreated water (such as river, lake, or ground water). Q1 contains organic and inorganic particles that need to be removed. Q2 comprises a flocculating agent. S1 can be typically a settling tank (also known as sedimentation tank or clarifier) that removes particles based on gravity settling. S1 can also be a flotation tank that removes particles by floating them up to the surface of the tank. Q4 corresponds to collected solids or sludge. Q5 is effluent water that continues to the next treatment step. S2 comprises an in-line UV-vis spectrophotometer. An alarm can follow that is switched on automatically if a predetermined/preset polymer concentration is exceeded. If this happens, the polymer added to Q1 can be lowered automatically through S3 and S4 (optional). The remainder of the components are as defined above.

For embodiments (2) to (8), components not specifically described are similar to those outlined for (1).

2) Domestic Wastewater (sewage): In this application, Q1 is domestic wastewater (sewage) that contains organic and inorganic particles that need to be removed. S1 is a primary settling tank, secondary settling tank, or tertiary settling tank.

3) Industrial Wastewater: In this application, Q1 is industrial wastewater coming from an industrial process (such as food industry, beverage industry, textiles, manufacturing etc.) that contains organic and inorganic particles that need to be removed. S1 is a primary settling tank, secondary settling tank, or tertiary settling tank.

4) Environmental remediation/contaminated site clean up: During such a process, polymers can be used and they must be measured and controlled so as not to exceed predetermined concentrations. In this embodiment, Q1 can be contaminated wetland water, and S1 can be a settling tank.

5) Drinking water sludge: In this application, Q1 is sludge generated from drinking water treatment, and S1 is a thickener or a settling tank for sludge.

6) Domestic wastewater (sewage) sludge: In this application, Q1 is sludge generated from domestic wastewater treatment, and S1 is a thickener, a settling tank, or a flotation tank for wastewater sludge.

7) Industrial wastewater sludge: In this application, Q1 is sludge generated from industrial wastewater treatment, and S1 is a thickener, a settling tank, or a flotation tank for industrial sludge.

8) Tailings from gas, oil, and mining industries: In this application, Q1 is tailings generated from gas, oil, and mining industries. S1 is a gravity thickener or a reservoir.

FIG. 11 illustrates yet another embodiment of the present application, wherein Q1 is a liquid or slurry stream, Q2 is a treatment agent stream or liquid or slurry stream carrying the treatment agent, and Q3 is a liquid or slurry stream mixed with the treatment agent. S1 represents a separation device which separates the incoming stream to liquid-rich (Q5) and solid-rich (Q4) streams. Q6 is a liquid-rich stream in communication with components S2, S3, S4, and S5 defined below. S5 is a separation device connected to the liquid-rich stream that removes the organic and inorganic particles and solids from the liquid-rich stream. S2 is a sensor connected to the liquid-rich stream after S5 that produces a response based on measured absorbance or a related value such as transmittance. Based on the measured absorbance or related value of the liquid-rich stream, S2 produces a signal which is transmitted to controller S3. Controller S3 using, for example, a preprogrammed algorithm determines an appropriate response for flow control device S4 to control the entering flow of the treatment agent. S4 responds to the signal from S3 and controls or regulates the flow of treatment agent entering to flow Q3.

With respect to component S5, such separation devices are known to those of skill in the art. For instance, quick spin or vortex filters could be used, or a centrifuge or filtration system.

Other variations of the above polymer dose measurement and optimization systems are possible. For example, separation device S5 and sensor S2 can be located right before the main separation device S1 or right after S1 or both. Additional sensors, controllers, flow control and separation devices can be added to the systems along the flow streams Q1, Q2, Q3, Q4, Q5 and Q6.

It is to be understood that a variety of configurations can be used in embodiments of the present application. For example, multiple sensors or controllers can be used to control the flow of treatment agent into the system. Signals from outside of the system can also be used to control or direct addition of treatment agent. For example, a process located upstream can transmit an appropriate signal to controller S3. Controller S3 can then utilize this information to determine an appropriate response for flow control device S4. Thus, the treatment systems, as described herein, can be modified as desired for a particular process.

In some cases, systems of the present application can include additional components beyond those specifically illustrated. Dilution of samples prior to measuring their absorbance in the UV-vis range may be required, and can be accomplished by, for example, using an in-line system and a clean water source As well, additional process streams can also enter into the system, or mixing of an incoming process stream and the treatment agent stream can occur within a separation device. The separation device may also produce additional streams other than the streams described above, or other unit operations can be located within the treatment system.

To gain a better understanding of the invention described herein, the following examples are set forth. It should be understood that these examples are for illustrative purposes only. Therefore, they should not limit the scope of this invention in any way.

EXAMPLES

Example 1

Measurement of Polymer Concentration Using Ultraviolet-Visible (UV-Vis) Spectroscopy The goal of this study was to develop a method that uses UV-vis spectroscopy for the determination of residual polymer concentration. Specifically, the goal of this study was to develop a quick and simple method for the measurement of residual polymer concentration in water and sludge centrate using UV-vis spectroscopy. This successful method can be adopted for polymer dose optimization and development of a dewatering automation system at water and wastewater treatment plants, for example.

Materials and Methods
Polymers

Five cationic polymers, commonly used in sludge dewatering, were used in the experiments. The polymers and their characteristics, including approximate charge densities and molecular weights, are listed in Table 1.

TABLE 1

| Characteristics of cationic polymers | | | |
|---|---|---|---|
| Polymer Name | Charge Density | Molecular Weight | Physical Form |
| CIBA Zetag 7587 | High | High | Free-flowing microbead |
| SNF Flo Polymer CA 475 | High | Ultra-high | Granular solid |
| SNF Flo Polymer CA 4400 | Low | Very-high | Granular solid |
| SNF Flo Polymer CA 4600 | High | Very-high | Granular solid |
| SNF Flo Polymer CA 4800 | Very-high | Ultra-high | Granular solid |

All of the polymers listed in Table 1 are polyacrylamide polymers. The Zetag polymer was chosen since it is the polymer used for sludge dewatering at the local wastewater treatment plant. The SNF polymers were chosen in order to represent cationic polymers with a range of charge densities and molecular weights. These five polymers exhibit a wide range of polymer characteristics, and were tested in the UV-vis range.

Polymers were prepared to a concentration of 0.05% for use in the experiments. The polymers were prepared using a jar test apparatus (Phipps and Bird, USA) by mixing dried polymer in 500 mL of deionized water at a speed of 200 rpm for 5 minutes, followed by mixing at a speed of 125 rpm for 55 minutes to ensure that the solution was well-mixed. After the initial 1-hour of mixing, the solutions were mixed with a hand-held blender for ten seconds, and left to sit for 1 hour before use in the experiments. This procedure produced a homogeneous and well-mixed polymer solution for all of the polymers used in the experiments. Polymer stock solution was prepared daily.

Samples

Two water matrices were analyzed in the experiments. The first water matrix was deionized (DI) water (Millipore Direct Q UV 3, Millipore, USA). The other matrix was the centrate of anaerobically digested sludge collected from a wastewater treatment plant. The centrate was used in the experiments as it is and also after filtration through a 0.45 µm filter. Centrate samples were diluted at different ratios so that the final samples had 10, 20, 25, 50 and 100% centrate in them.

Absorbance Measurements

Absorbance measurements were performed with a bench-top UV-Vis spectrophotometer (Cary 100 Bio UV-Vis Spectrophotometer, Varian Inc./Aligant Technologies, Canada) using a 1 cm quartz glass cell (Hellma Canada Ltd., Canada). Initial scans showed no change in the absorbance measurements between 300 and 800 nm, and 190-300 nm wavelength range was used in the experiments. Each measurement was repeated three times, and the reported absorbance measurements are the average of three replicates. Eight replicates were used to determine the method detection limit as explained in Bertheroux and Brown (2003).

Results and Discussion

Measurement of Polymer Concentration in Water

Relationship between polymer dose and UV absorbance was evaluated using five different polymers spiked to different concentrations in deionized water. Absorbance scans are shown in FIG. 1 a, b, c, d, e (0-20 mg/L) and FIG. 2 a, b, c, d, e (20-100 mg/L) for the five polymers. Overall, the shapes of the absorbance scans were similar between the different polymers. For all polymers, increasing the polymer concentration resulted in an increase in the absorbance values, and the highest absorbance values were measured at 200 nm. Similar results were also obtained at 190 nm. At higher wavelengths, absorbance values substantially dropped by 220 nm and there was no significant difference between the absorbance values beyond 240 nm between different polymer concentrations. The difference between absorbance values after each incremental polymer increase was highest at 200 nm. The absorbance values measured at 200 nm were similar for each polymer, and were between an absorbance of 0.2 and 0.3 for a polymer concentration of 20 mg/L.

Based on the results shown in FIGS. 1 and 2, it appeared that a linear relationship between absorbance and polymer concentration could be established at wavelengths 200, 210 and 220 nm. When absorbance values were plotted against polymer concentrations, a strong linear relationship was observed between absorbance and polymer concentration for each polymer (FIG. 3 a, b, c, d, e) in the low concentration range (0-20 mg/L). A strong linear relationship was also obtained at 190 nm. $R^2$ values and slopes for the regression lines are provided in Table 2. The slopes of the regression lines were highest at 200 nm indicating that this would be the wavelength that is most sensitive to changes in the polymer dose. Majority of the $R^2$ values were >0.9, and the lowest $R^2$ value was 0.816. At 200 nm, $R^2$ values were 0.938, 0.999, 0.999, 0.995, and 0.992 for the polymers Zetag, SNF 475, SNF 4400, SNF 4600, and SNF 4800 respectively.

A strong linear relationship between absorbance and polymer concentration was also observed in the high concentration range (20-100 mg/L) for each polymer at wavelengths 200, 210 and 220 nm (FIG. 4 a, b, c, d, e). Majority of the $R^2$ values were >0.9, and the lowest $R^2$ value was 0.851 (Table 2). At 200 nm, $R^2$ values were 0.981, 0.999, 0.999, 0.999, and 0.998 for the polymers Zetag, SNF 475, SNF 4400, SNF 4600, and SNF 4800 respectively. The results indicated that the absorbance measurements at 200 nm could be used to measure the polymer concentrations both at low and high polymer doses. In contrast, there was less variability between the absorbance values at a wavelength of 220 nm.

TABLE 2

Linear regression values from calibration curves

|  | Concentration Range (mg/L) | $R^2$ 200 nm | $R^2$ 210 nm | $R^2$ 220 nm | Slope 200 nm | Slope 210 nm | Slope 220 nm |
| --- | --- | --- | --- | --- | --- | --- | --- |
| Zetag | 0-20 | 0.938 | 0.864 | 0.988 | 0.007 | 0.004 | 0.001 |
|  | 20-100 | 0.981 | 0.851 | 0.995 | 0.003 | 0.001 | 0.001 |
| SNF 475 | 0-20 | 0.999 | 0.993 | 0.997 | 0.008 | 0.004 | 0.001 |
|  | 20-100 | 0.999 | 0.999 | 0.999 | 0.006 | 0.003 | 0.001 |
| SNF 4400 | 0-20 | 0.999 | 0.999 | 0.999 | 0.009 | 0.003 | 0.001 |
|  | 20-100 | 0.999 | 0.999 | 0.999 | 0.008 | 0.003 | 0.001 |
| SNF 4600 | 0-20 | 0.995 | 0.981 | 0.996 | 0.008 | 0.004 | 0.001 |
|  | 20-100 | 0.999 | 0.999 | 0.999 | 0.007 | 0.003 | 0.001 |
| SNF 4800 | 0-20 | 0.922 | 0.816 | 0.979 | 0.006 | 0.003 | 0.001 |
|  | 20-100 | 0.998 | 0.997 | 0.998 | 0.004 | 0.002 | 0.001 |
| Composite | 0-20 | 0.953 | 0.865 | 0.964 | 0.008 | 0.004 | 0.001 |
|  | 20-100 | 0.731 | 0.749 | 0.931 | 0.006 | 0.002 | 0.001 |

Although a strong linear relationship between polymer concentration and absorbance of samples exist in the concentration range of 0-20 mg/L, the sensitivity or the detection limit of the method at very low concentrations also needs to be established. Method Detection Limit (MDL) is the minimum concentration of a substance that can be measured and reported with 99% confidence that the analyte concentration is greater than zero, and is determined from analysis of a sample in a given matrix containing the analyte. The MDL for the Zetag polymer in deionized water was calculated using the EPA method presented in Bertheroux and Brown (2003). Among the 5 polymers tested, Zetag polymer was chosen as the most challenging polymer as it showed the lowest linearity ($R^2$=0.938 at 200 nm, $R^2$=0.864 at 210 nm, and $R^2$=0.988 at 220 nm) compared to other polymers. The method detection limits were found to be 0.55 mg/L at 200 nm, 0.61 mg/L at 210 nm, and 1.98 mg/L at 220 nm. It should be noted that the detection limits may vary with different polymers, and using the specific absorbance maxima for each polymer would increase the sensitivity of the method and lower the detection limit. For polymers used in water and wastewater treatment, the absorbance maxima are expected to be in the range of 190-240 nm. Although the detection limit of 0.55 mg/L at 200 nm is higher than the detection limits reported using more sophisticated methods (i.e., NMR analysis or SEC analysis), the detection limit is adequate for measuring residual polymer concentrations. For example, NMR analysis of filtrate from a digested sludge dewatering process at a wastewater treatment plant yielded a detectable polymer concentration of approximately 8.0 mg/L of polymer (Chang et al., 2002).

Figure 5A:
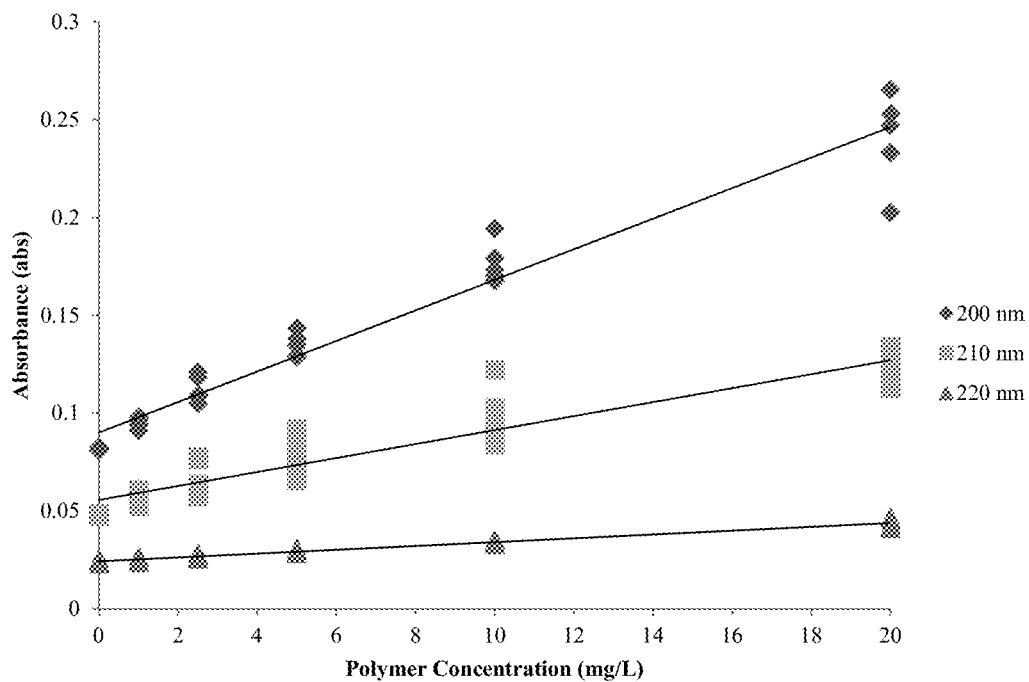
FIG. 5a graphically depicts a composition calibration curve of absorbance versus concentration (0 to 20 mg/L) obtained by combining the results depicted in FIG. 3 for all five polymers (Zetag polymer; SNF 475; SNF 4400; SNF 4600; and SNF 4800).
Figure 5B:
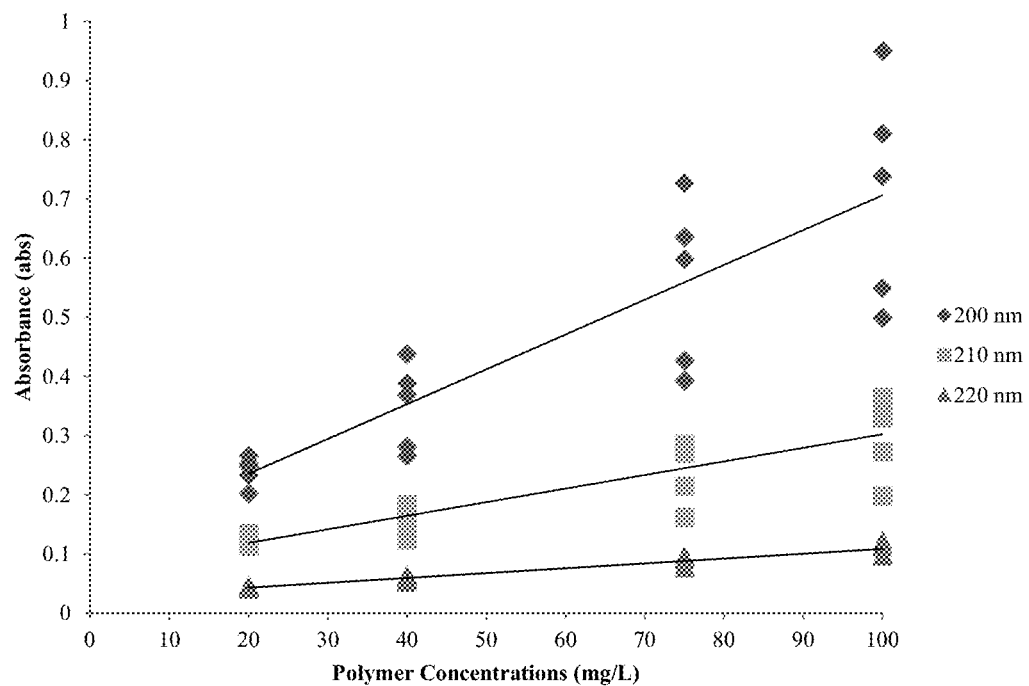
FIG. 5b graphically depicts a composition calibration curve of absorbance versus concentration (20 to 100 mg/L) obtained by combining the results depicted in FIG. 4 for all five polymers (Zetag polymer; SNF 475; SNF 4400; SNF 4600; and SNF 4800).

Combining the results from all five polymers, a composite calibration curve was determined for the low concentration range (FIG. 5a) and the high concentration range (FIG. 5b). The composite curve was more accurate between 0-20 mg/L polymer at the wavelengths of 200 nm, 210 nm, and 220 nm, with $R^2$ ranging from 0.86-0.94 (Table 2). In comparison, the composite curve was less accurate between 20-100 mg/L polymer with $R^2$ ranging from 0.73-0.91. Therefore, the composite curve could provide a reasonable estimation when the polymer concentration is expected to be between 0-20 mg/L for a variety of polymers.

Measurement of Polymer Concentration in Sludge Centrate

The method was also evaluated using centrate which was collected from a wastewater treatment plant. The polymer that was spiked in centrate was the Zetag polymer, as this is the polymer that is presently used at the treatment plant for sludge dewatering.

Figure 6A:
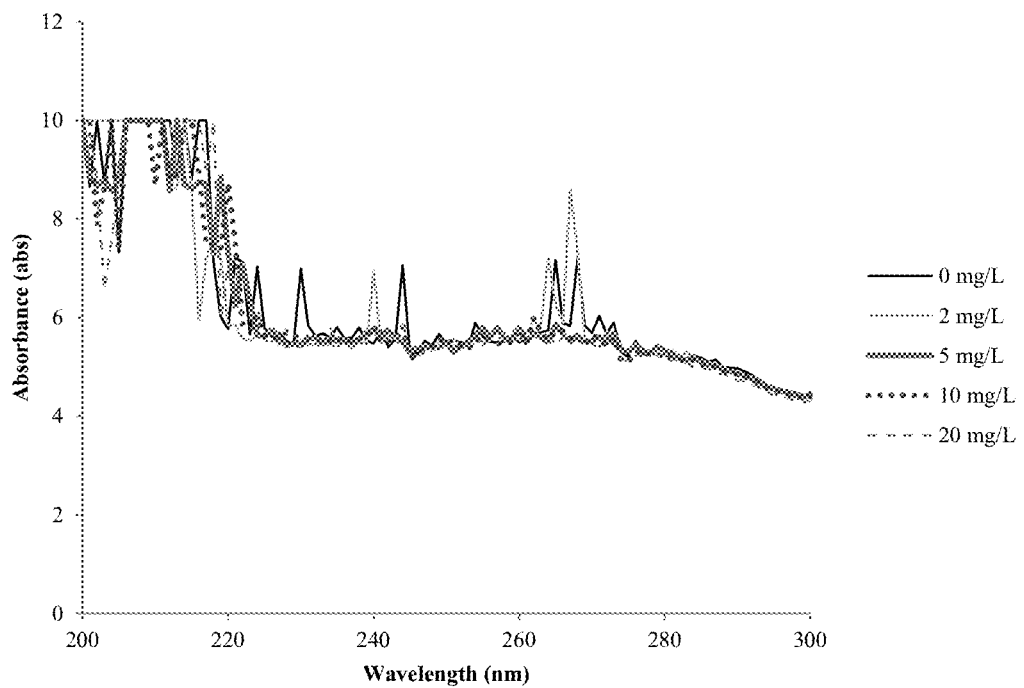
FIG. 6 depicts absorbance scans between 200 nm and 300 nm of various dilutions of centrate collected from a wastewater treatment plant, and spiked with Zetag polymer at a range of concentrations between 0 mg/L and 20 mg/L: (a) 100% centrate; (b) 50% centrate; (c) 25% centrate; (d) 20% centrate: and (e) 10% centrate.
Figure 6B:
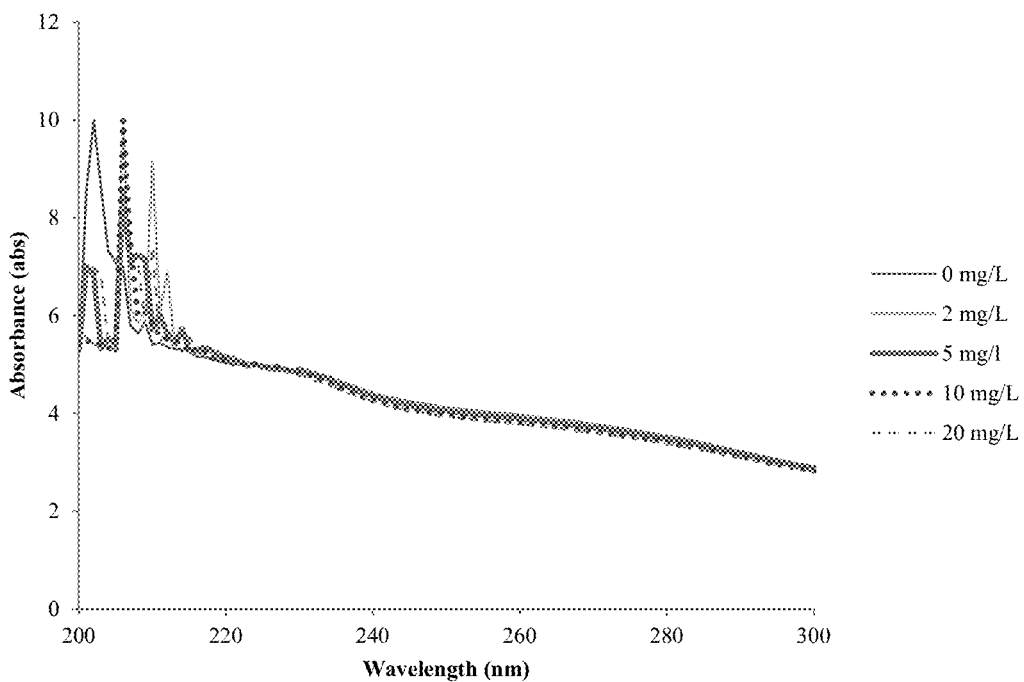
Figure 6C:
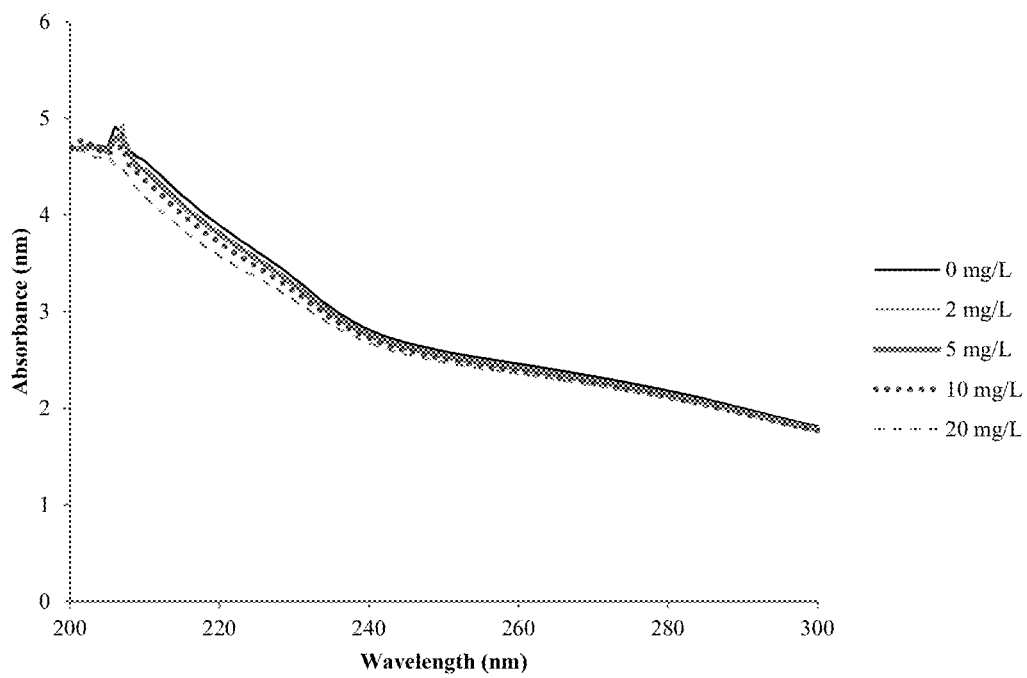
Figure 6D:
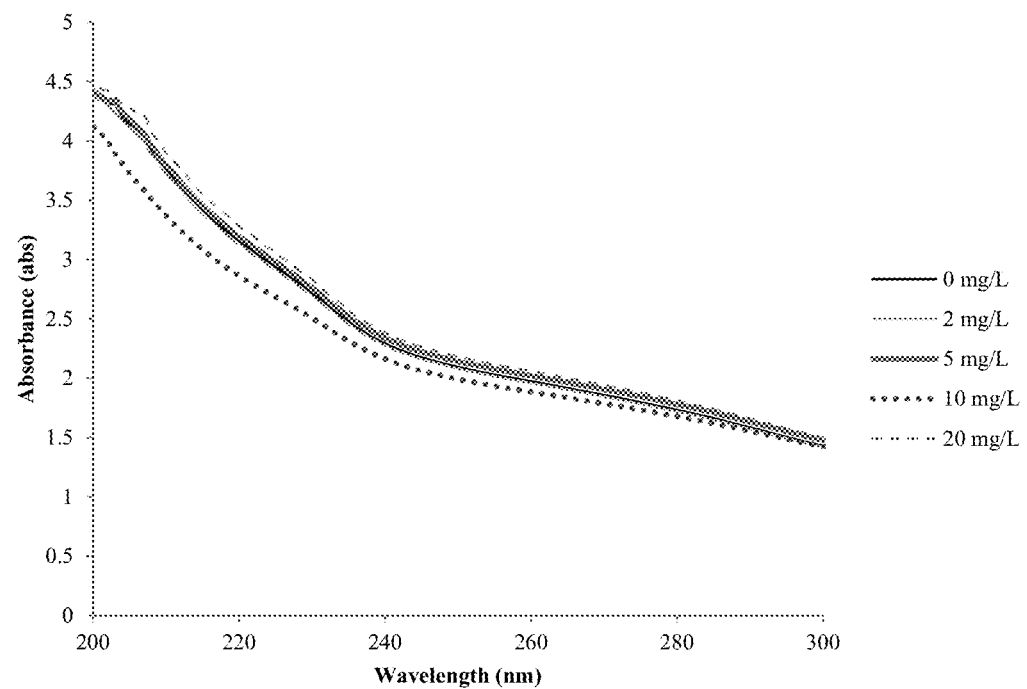
Figure 6E:
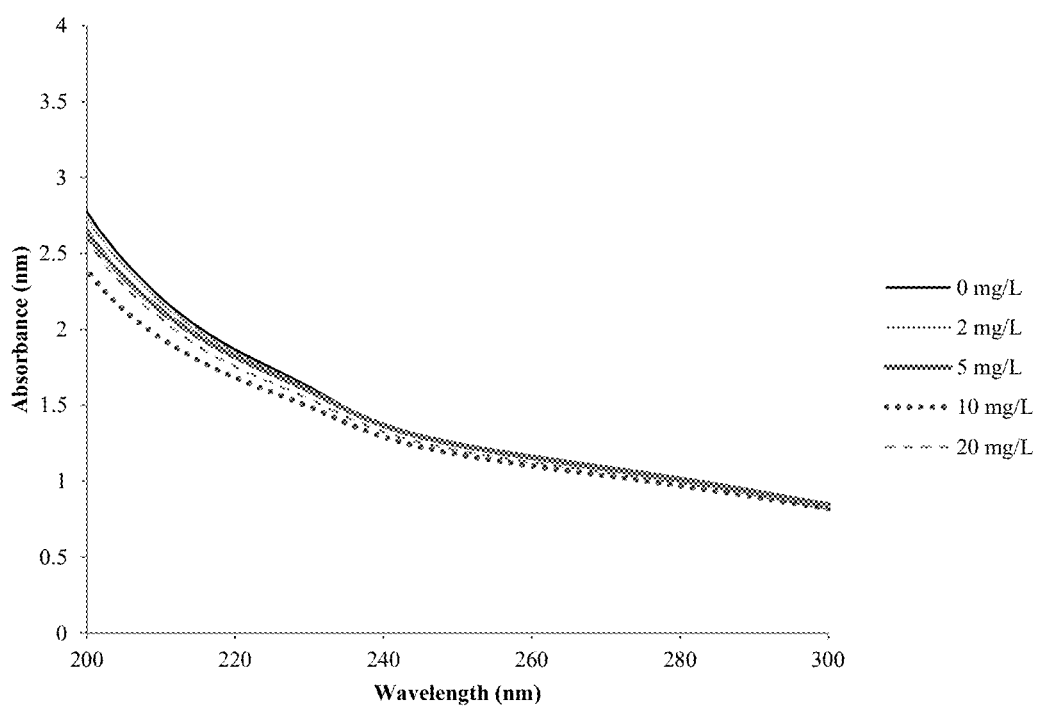

The centrate exhibited very high absorbance exceeding the working range suggested for the instrument (past 4 Abs) (FIG. 6a). This necessitated the dilution of centrate samples with deionized water prior to absorbance measurements. When centrate was diluted by 50%, the absorbance values were still very high and exhibited random spikes (FIG. 6b). Samples containing 25%, 20%, and 10% centrate produced good absorbance scans and the absorbance values were within the working range of the instrument (FIG. 6c, d, and e). However, the results obtained from centrate were not similar to the results obtained from deionized water (FIG. 1). Even at the lowest dilution of 10% centrate (FIG. 6e), the results appeared reversed, with 0 mg/L polymer achieving the highest absorbance. This trend, which is consistent throughout FIG. 6, where the lowest polymer concentrations in centrate yield absorbance results that are similar to those observed at higher polymer concentrations in water is likely caused by the removal of suspended matter and particles in centrate after the addition of polymer. Addition of polymer would result in flocculation and settling out of suspended particles which would decrease the overall absorbance of the samples. This indicated that the suspended matter should be removed from centrate first before taking the absorbance readings in order to accurately determine the residual polymer concentrations. This can simply be achieved with filtration or centrifugation.

Figure 7A:
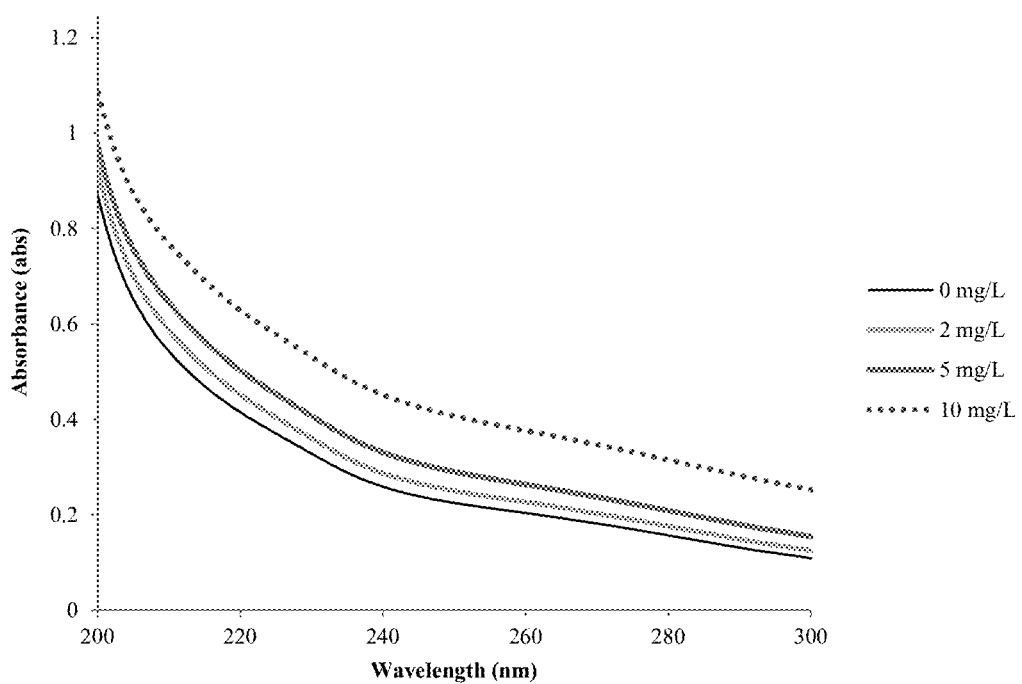
FIG. 7 depicts absorbance scans between 200 nm and 300 nm of centrate collected from a wastewater treatment plant that has been filtered through a 0.45 µ filter, diluted to (a) 10%; and (b) 25%; and spiked with Zetag polymer at a range of concentrations between 0 mg/L and 10 mg/L.
Figure 7B:
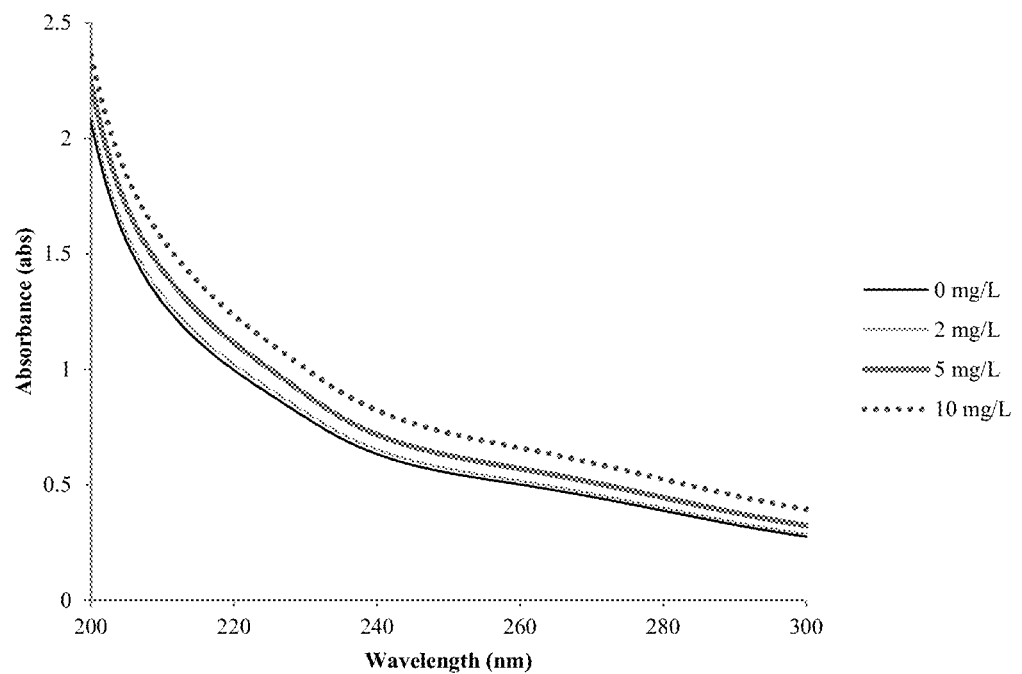
Figure 8A:
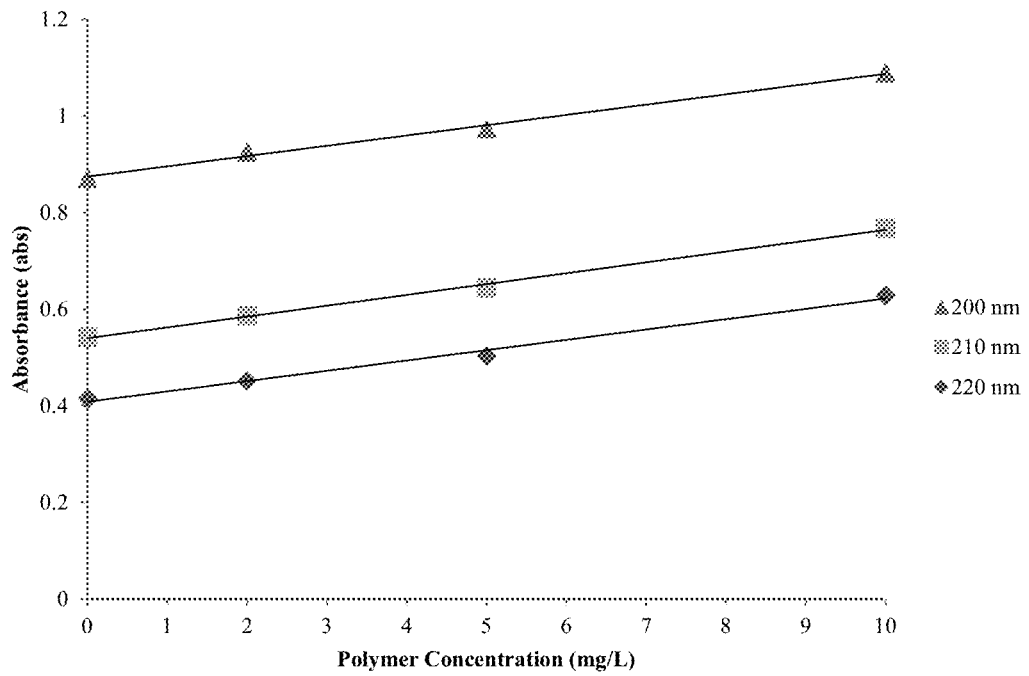
FIG. 8 graphically depicts the relationship between absorbance and Zetag polymer concentration at 200 nm, 210 nm, and 220 nm in centrate collected from a wastewater treatment plant that has been filtered through a 0.45 µ filter, diluted to (a) 10%; and (b) 25%; and spiked with Zetag polymer at a range of concentrations between 0 mg/L and 10 mg/L.
Figure 8B:
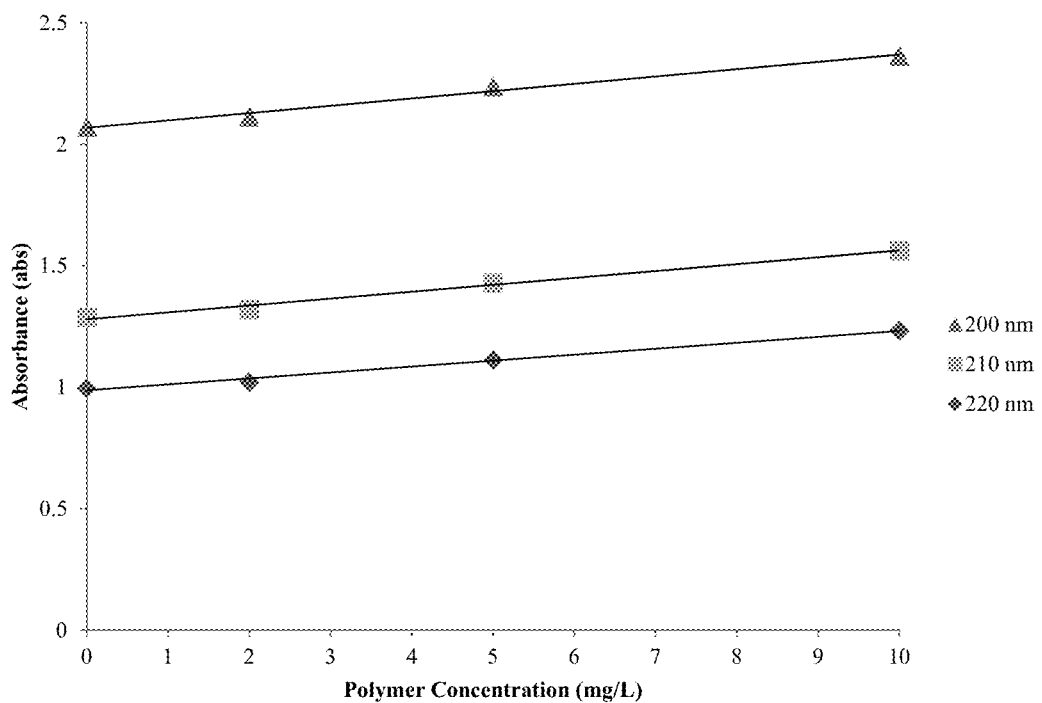

For the next experiments, centrate was first filtered through a 0.45 µ filter and then diluted by deionized water to 10% and 25% centrate. A very low concentration range of 0-10 mg/L was chosen since this is the most challenging concentration range that would test the sensitivity of the method. It should be noted that there was likely some residual polymer present in the centrate collected from the treatment plant, and the added polymer concentrations (0, 2, 5 and 10 mg/L) were in addition to the initial residual polymer concentration. The resulting absorbance scans are illustrated in FIG. 7a for 10% centrate and in FIG. 7b for 25% centrate. Similar to the results previously observed (FIG. 1), increasing the polymer dose incrementally increased the measured absorbance and the highest absorbance was measured at 200 nm. Presence of dissolved organic matter in the centrate did not interfere with the measurements. Dissolved organic matter highly absorbs UV light around 254 nm which is unlikely to interfere with the polymer absorbance measurements at wavelengths around 200 nm. When absorbance values were plotted against polymer concentrations, a strong linear relationship was observed for both the 10% and 25% centrate samples (FIG. 8 a and b). The $R^2$ values at 200 nm were 0.995 and 0.988 respectively (Table 3). These results showed that the method could also be used successfully in centrate samples.

TABLE 3

Linear regression values for Zetag polymer in filtered and diluted centrate

|  | | $R^2$ | | | Slope | |
| --- | --- | --- | --- | --- | --- | --- |
| Concentration Range (mg/L) | 200 nm | 210 nm | 220 nm | 200 nm | 210 nm | 220 nm |
| 10% centrate dilution | 0-10 | 0.995 | 0.997 | 0.991 | 0.021 | 0.022 | 0.021 |
| 25% centrate dilution | 0-10 | 0.988 | 0.992 | 0.992 | 0.03 | 0.028 | 0.024 |

Conclusions

A new method was developed to measure the polymer concentration in liquids and slurries using UV-vis spectroscopy. Specifically, UV-vis spectroscopy was successfully used in determining polymer concentrations in water and centrate samples. Five different polymers were tested and a strong linear relationship was established between absorbance values and polymer concentrations in the low (0-20 mg/L) and high (20-100 mg/L) polymer ranges in the UV-vis range. The incremental increases in polymer concentrations corresponded to incremental increases in absorbance measurements. The method was also sensitive at very low polymer concentrations (<10 mg/L), and the method detection limit (MDL) for the Zetag polymer was determined as 0.55 mg/L at 200 nm. It should be noted that the detection limits may vary with different polymers, and using the specific absorbance maxima for each polymer would increase the sensitivity of the method and lower the detection limit.

The method provides a quick and simple tool for directly measuring polymer concentrations, and it is useful for both research and practice. The method can be applied to water and wastewater samples as well as to slurries such as water and wastewater treatment sludges.

The method is expected to find future applications in various fields that require the use and optimization of polymers for the separation of solids and particles from a liquid or slurry stream. One promising application is the optimization of polymer dose at water and wastewater treatment plants using an in-line UV-vis spectrometer or a similar sensor. This study has shown that after pre-treatment of centrate, simple absorbance measurements can successfully determine low concentrations of polymer in sludge centrate which can be used for the optimization of polymer dose. Thus, the method provides a tool for not only measuring polymer concentration but also for the optimization of polymer dose.

Example 2

Measurement of Polymer Concentration Using Uv-Vis Spectroscopy in-Line and Real-Time in a Treatment Process The goal of this study was to test the performance and sensitivity of this method using an in-line UV-vis spectrophotometer that is developed for water quality monitoring at water and wastewater treatment plants and determine statistically established detection limits for a range of polymers in distilled water and sludge centrate. New generations of in-line spectrophotometers provide accurate measurements in real-time, and a successful method for in-line and real-time measurement of polymer concentration would find important applications in water and wastewater treatment plants.

Materials and Methods

Polymers

In the first phase of experiments, Hydrex 3572 (Veolia Inc.) was tested with distilled water to establish its detection limit and UV absorbance spectra. In the second phase, Hydrex 3572 and FloPolymer CB 4350 (SNF Inc.) were tested in centrate samples collected from a wastewater treatment plant. FloPolymer CB 4350 was the polymer that was used in the treatment plant. Hydrex 3572 is an anionic polyacrylamide polymer, and FloPolymer CB 4350 is a cationic polyacrylamide polymer.

Preparation of Stock Polymer Solution

Stock polymer solutions were prepared at a concentration of 0.01% for spiking in samples. The polymers were prepared using a jar test apparatus (Phipps and Bird, USA) by mixing 0.1 g polymer in 1,000 mL of deionized water at a speed of 220 rpm for 5 minutes, followed by mixing at a speed of 125 rpm for 55 minutes. After the initial 1-hour of mixing, the solution was mixed with a hand-held blender for 10 seconds, and left to sit for 1 hour before use in the experiments. This procedure produced a well-dissolved polymer solution for the polymers. Polymer stock solutions were prepared daily.

Dilution of Samples

The following dilution procedure was used for the centrate samples. First, the sample was spiked with polymer to give the desired polymer concentration. Then, the sample and polymer mixture was mixed for 2 minutes at 90 rpm and its absorbance spectrum was measured. Afterwards, the sample was diluted with distilled water at a ratio of 1:50, and its absorbance spectrum was measured again.

Absorbance Measurements

The in-line UV-vis spectrophotometer (Real Spectrum Platinum Series) used is manufactured by Real Tech Inc. (Ontario, Canada) and provides real-time analysis across the entire spectrum of UV and/or visible light. The instrument combines high wavelength resolution with the power of a deuterium light source as used in high-end lab spectrophotometers, and provides accurate and sensitive spectrum analysis. The spectral range is extended into the visible region with the addition of a tungsten light source. The instrument is commonly used at water and wastewater treatment plants for real-time and in-line measurement of total organic carbon, disinfection by-product precursors, nitrate, and UV transmittance for UV disinfection. The instrument has a sampling frequency of 1 minute and has a wavelength resolution of 1 nm. The recommended working range is between 0-1 AU.

In this study, the absorbance values were measured between 191.5-750 nm and no significant absorbance was detected from polymer samples above 260 nm. Therefore, the results are presented in the wavelength range of 191.5-300 nm.

Statistical Analysis

All experiment sets were repeated at least 3 times. For each triplicate, a newly prepared polymer stock solution was used. A minimum of 7 data points were recorded at each polymer concentration.

Detection limits were established using the US EPA (US Environmental Protection Agency) approved Method Detection Limit (MDL) as explained in Bertheroux and Brown (1993) Seven replicates were used to establish the detection limits. The MDLs for all polymers were determined at a 99% confidence level. Confidence intervals of the regression lines for calibration curves were 95%.

Results and Discussion

The experiments were carried out in two phases. In Phase I, distilled water was used to establish the minimum detection limit for Hydrex 3572. In Phase 2, centrate collected from a wastewater treatment plant was used to establish the minimum detection limits for Hydrex 3572 and FloPolymer CB 4350. For all samples, polymer concentrations were varied between 0.1 mg/L and 20 mg/L, and detection limits were established at 191.5, 200 and 210 nm.

Phase I: Detection Limits in Distilled Water

Figure 12A:
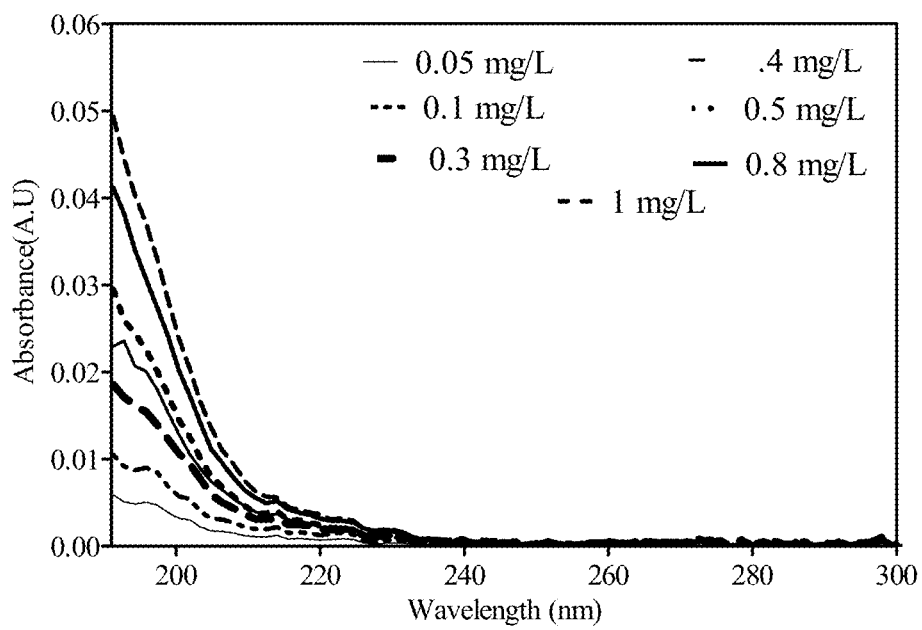
FIG. 12: (a) Absorbance spectra for Hydrex 3572 between 191.5 nm and 300 nm in distilled water at a concentration from 0.05 to 1 mg/L; and (b) linear regression of the sample absorbance at 191.5 nm and polymer concentration.
Figure 13A:
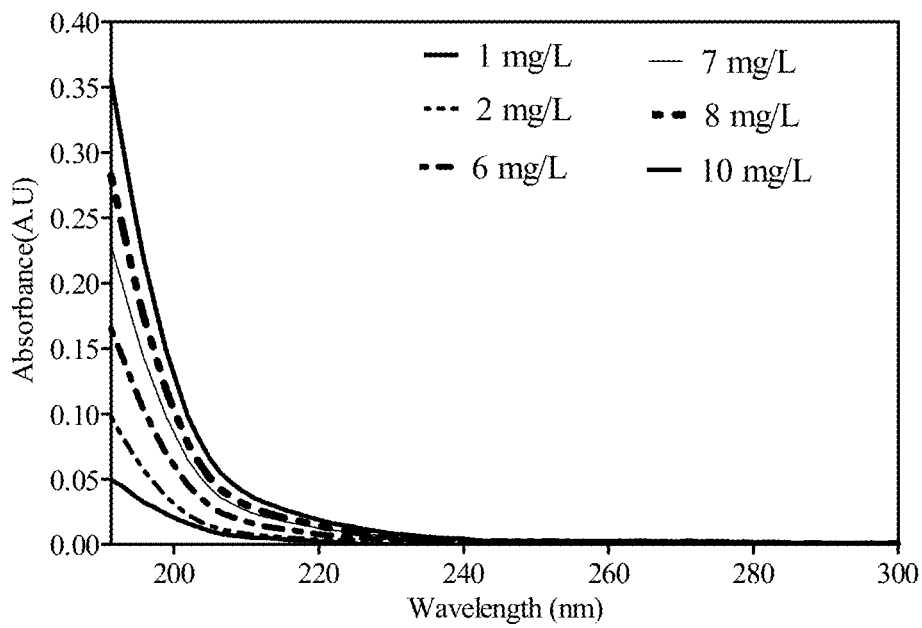
FIG. 13: (a) Absorbance spectra for Hydrex 3572 between 191.5 nm and 300 nm in distilled water at a concentration from 1 to 10 mg/L; and (b) linear regression of the sample absorbance at 191.5 nm and polymer concentration.
Figure 14A:
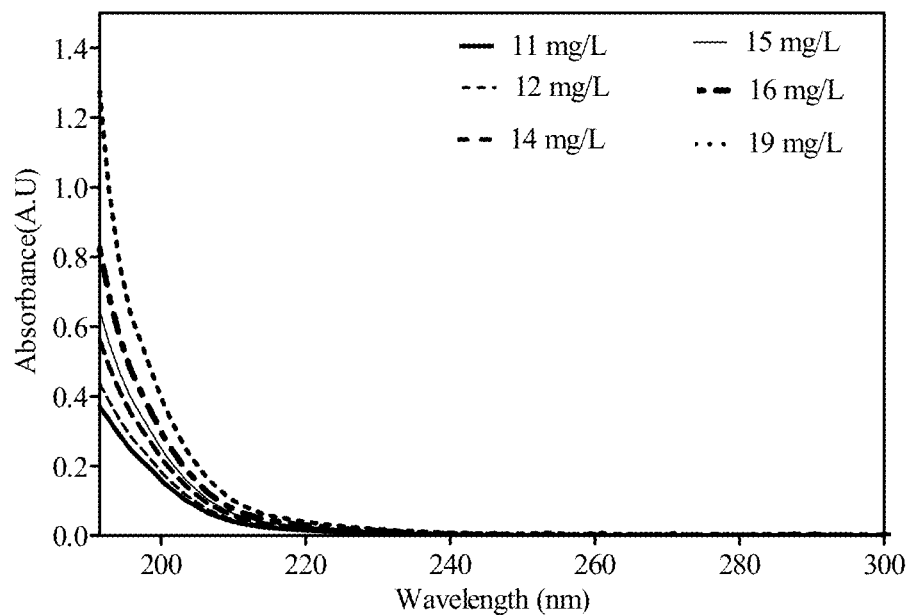
FIG. 14: (a) Absorbance spectra for Hydrex 3572 between 191.5 nm and 300 nm in distilled water at a concentration from 10 to 20 mg/L; and (b) linear regression of the sample absorbance at 191.5 nm and polymer concentration.

Absorbance spectra of Hydrex 3572 were determined in distilled water in three concentration ranges: 0.1-1 mg/L, 1-10 mg/L, and 10-20 mg/L (FIGS. 12(a), 13(a) and 14(a), respectively). The selected concentration ranges allow the determination of minimum detection limits for the polymer and also show the performance and sensitivity of the method at low, medium and high polymer concentrations. The absorbance measurements were performed in the wavelength range of 191.5-750 nm and the highest absorbance values were recorded at 191.5 nm. UV absorbance gradually decreased between 191.5-240 nm and there was no significant absorbance beyond 240 nm. Incremental increases in polymer concentrations resulted in incremental increases in absorbance values indicating a linear relationship between polymer concentration and UV absorbance of the samples. For Hydrex 3572, the absorbance values measured ranged from 0.01 to 1.2 (a.u) for the concentration range of 0.1 mg/L to 20 mg/L. Although the absorbance measurements for very low (<0.5 mg/L) polymer concentrations showed some noise, the in-line UV-vis spectrophotometer was still able to detect 0.1 mg/L increments of polymer increases.

Figure 12B:
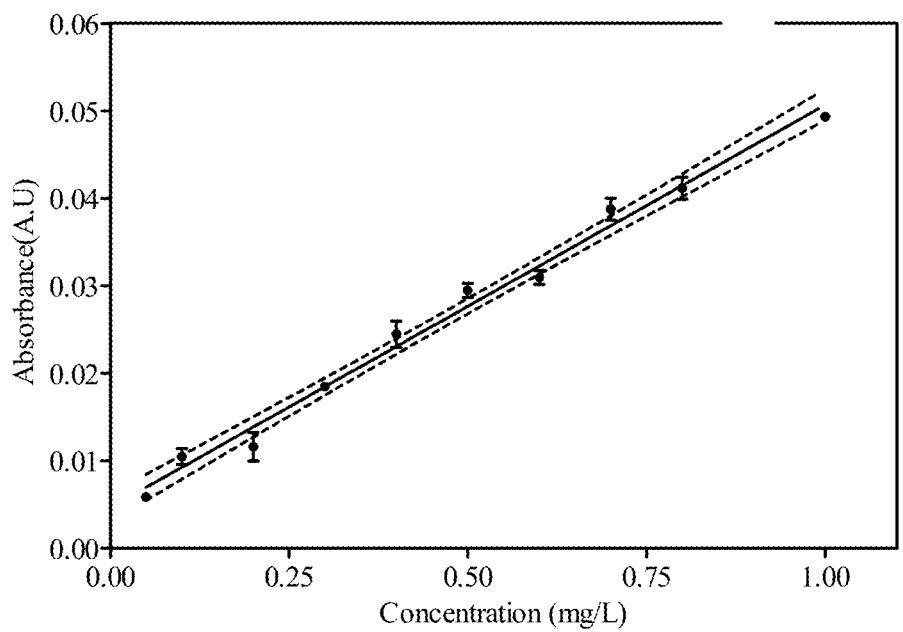
Figure 13B:
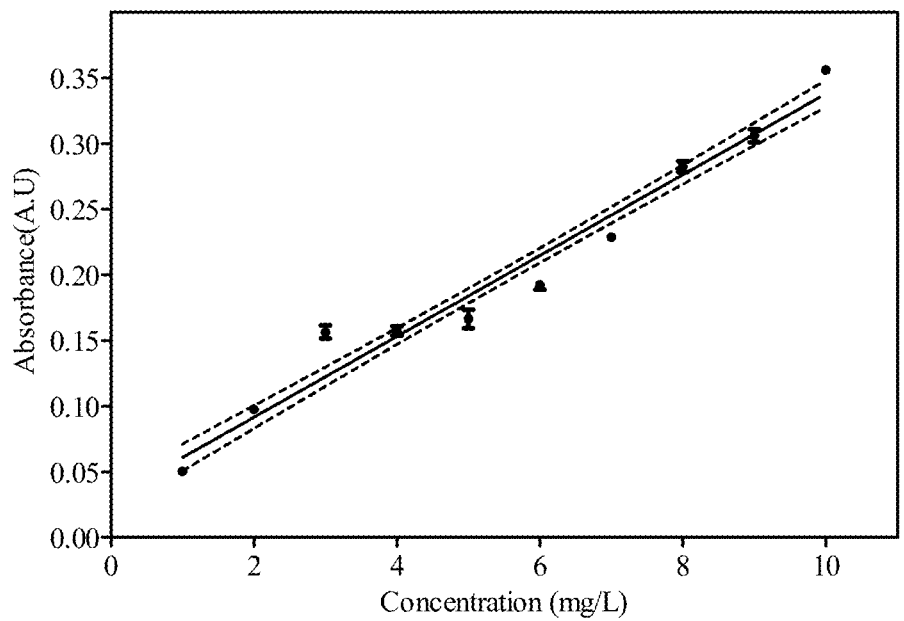
Figure 14B:
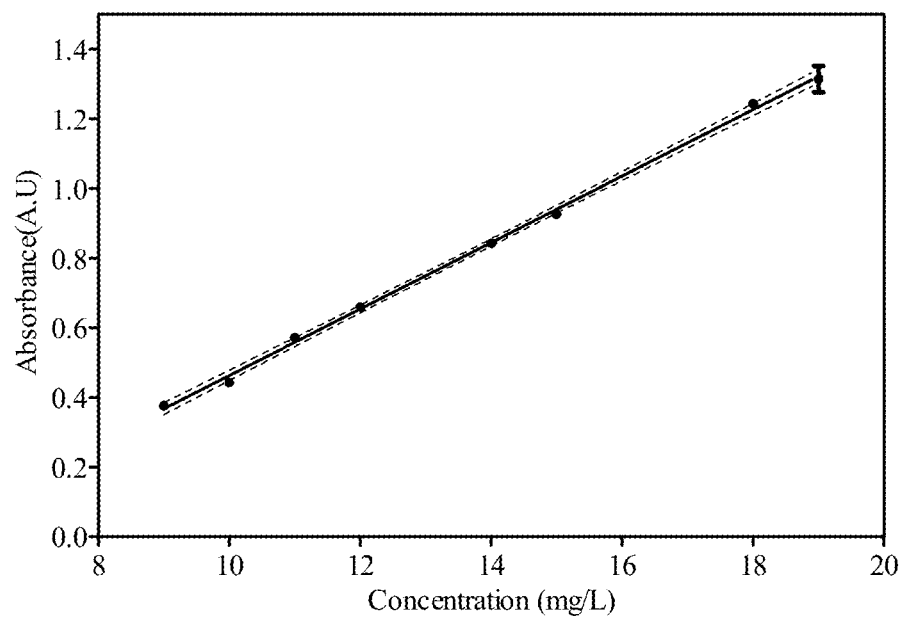

The linear relationship between the polymer concentration and sample absorbance allows the construction of a calibration curve to determine the unknown polymer concentrations in water. When the absorbance of water samples at 191.5 nm was plotted against the polymer concentration, a strong linear relationship based on a 95% conference interval (dashed lines) was found (FIGS. 12(b), 13(b) and 14(b)). Linear relationship between concentration and absorbance also held at 200 and 210 nm, but the slopes of the regression lines were lower indicating that the method would be less sensitive at these wavelengths. In addition, statistical analysis of the data demonstrated lower confidence intervals for regression lines at 200 and 210 nm.

Detection limits were established using the EPA approved MDL method. Since distilled water did not contain any organic or inorganic contaminants that absorb light, no dilution was needed. Detection limits were found as 0.25 mg/L at 191.5 nm, 0.89 mg/L at 200 nm and 1.3 mg/L at 210 nm for the Hydrex polymer. This shows the very high sensitivity of the absorbance measurements at 191.5 nm.

Phase 2: Establishing Detection Limits in Centrate

Detection Limits in Centrate Collected from a Wastewater Treatment Plant

Known concentrations of polymers Hydrex 3572 and FloPolymer CB 4350 were spiked in centrate collected from a treatment plant. Centrate was used as it is without any pretreatment (e.g. removal of suspended solids). FloPolymer CB 4350 is the polymer that is currently used at Treatment Plant A. Preliminary testing indicated that dilution was needed due to the high absorbance of the centrate, and samples were diluted with distilled water at a ratio of 1:50. It should be noted that centrate had a strong yellowish color likely due to the ferric products used during treatment. The polymer concentration was varied from 0.1 to 10 mg/L.

Figure 15:
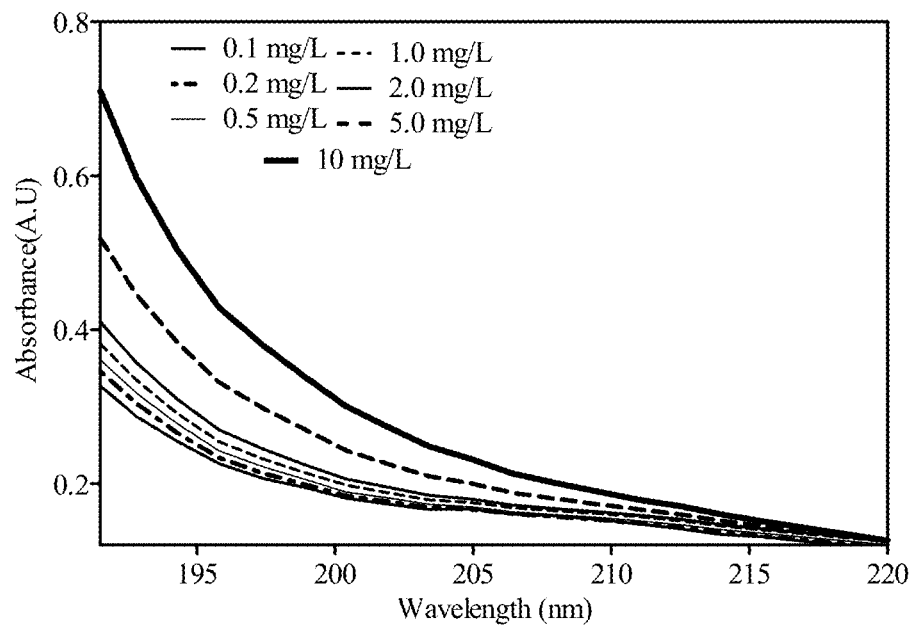
FIG. 15 depicts absorbance spectra of FloPolymer CB 4350 polymer in centrate at a dilution ratio of 1:50.

FIG. 15 shows the centrate absorbance at different FloPolymer CB 4350 concentrations using a 1:50 dilution ratio. Maximum absorbance values were again obtained at 191.5 nm. It can be seen that polymer concentrations as low as 0.2 mg/L could be detected with the spectrophotometer, but no significant difference was observed below 0.2 mg/L.

Figure 16:
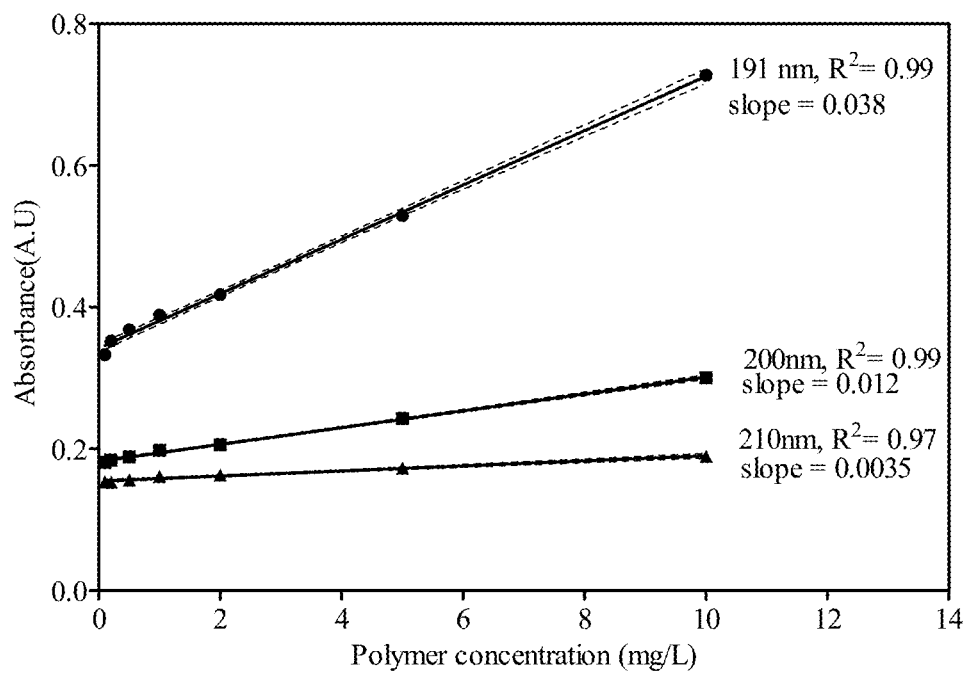
FIG. 16 graphically depicts linear regression of the sample (centrate) absorbance and polymer concentrations of FloPolymer CB 4350 polymer at 191.5, 200, and 210 nm.

The linear relationship between the centrate absorbance and the polymer concentration was observed at three selected wavelengths (191.5 nm, 200 nm and 210 nm) (FIG. 16). The dotted lines show the 95% confidence intervals. Since the absorbance of the samples were highest at 191.5 nm, the slope of the regression lines were also highest at 191.5 nm suggesting that this would be the wavelength that is most sensitive to changes in the polymer concentration. Calculations carried out with FloPolymer CB 4350 resulted in MDL values of 0.35 mg/L at 191.5 nm, 0.78 mg/L at 200 nm, and 1.1 mg/L at 210 nm. MDL values for Hydrex 3572 in centrate were found as 0.25 mg/L at 191.5 nm, 0.89 mg/L at 200 nm, and 1.3 mg/L at 210 nm.

Conclusions

This is the first study that demonstrates a method for in-line and real-time measurement of polymer concentration. Specifically, this study presents a method for in-line and real-time measurement of polymer concentration in water and centrate samples that is based on UV-vis spectrophotometry. The method is quick, simple and accurate, and can detect as low as 0.05 mg/L polymer. The method is likely to find applications in water and wastewater treatment plants and other industrial facilities that require measuring and adjusting polymer concentration on a continuous basis. The method would also be beneficial in preventing the excessive use of polymers and reducing their toxic effects on aquatic ecosystems.

Overall, the results from this study indicate that polymers used for water and wastewater treatment strongly absorb light in the 191.5-230 nm wavelength range, and the peak absorbance was measured at 191.5 nm for the polymers tested. Incremental increases in polymer concentrations resulted in incremental increases in absorbance values, and a strong linear relationship ($R^2 > 0.97$) between concentration and absorbance held at 191.5, 200 and 210 nm for the polymers. The detection limits depended on polymer type and chemistry. In addition, presence of organic and inorganic impurities in water samples impacted the detection limits. In distilled water samples, the lowest detection limit measured was 0.05 mg/L. The lowest detection limit measured in centrate samples collected from a wastewater treatment plant was 0.25 mg/L. The in-line UV-vis spectrophotometer used in this study provided a powerful tool for accurate and sensitive measurement of polymer concentration.

Example 3

Optimization of Polymer Dose in a Sludge Dewatering Process

Jar test experiments were performed with two different anaerobically digested sludge samples and polymers. Sludge samples were collected from Ottawa and Gatineau treatment plants and were conditioned with polymers that are used at these treatment plants (CA475 and CAB4500, both of which are cationic, polyacrylamide polymers). Polymer stock solutions had a concentration of 0.25%. Polymer dose was increased gradually using a jar-tester set-up with 100 mL of sludge sample, and lab-scale dewatering tests such as capillary suction time (CST) and filtration were carried out according to the Standard Methods (APHA, 1995). The lower the CST value, the better the dewaterability. The higher the filtrate volumes obtained after filtration, the better the dewaterability.

Absorbance measurements were conducted using an in-line UV-vis spectrophotometer (Real Spectrum Platinum Series) manufactured by Real Tech Inc. (Ontario, Canada). As can be observed in FIGS. 17 and 18, highest filtrate volume, lowest CST and lowest absorbance at 191.5 nm nicely align to indicate the optimum polymer dose. One can also see that if the optimum dose is exceeded, dewaterability worsens (increase in CST, decrease in filtrate volume).

The initial decrease in absorbance (at 191.5 nm) is due to aggregation and settling out of suspended particles. The optimum dose is where the lowest absorbance values are measured. Past this point, the absorbance values start increasing due to excess polymer (over dose range). This relationship is readily programmable into a full-scale automation package (e.g. using a minimum search algorithm).

Example 4

Measurement of Concentrations of Additional Flocculating Agents Using Ultraviolet-Visible (Uv-Vis) Spectroscopy Experiments similar to those conducted with the polymers in Example 1 were repeated with five other flocculating agents commonly used in sludge dewatering, namely, PolyDADMAC (Hydrex 6783) and a polyamine polymer (Hydrex 6704), and the inorganic conditioning agents ferric chloride, ferrous chloride, and alum.

For the PolyDADMAC polymer, 4 mL of a 20% by weight stock polymer solution was mixed in 1.5 L distilled water for 1 hour (resulting in a 0.053% by weight solution of polymer). For the polyamine polymer, 2 mL of a 50% stock polymer solution was mixed in 1 L distilled water for 1 hour (resulting in a 0.01% by weight solution of polymer). Increasing quantities (0.1, 0.2 . . . 32 mL) of the polymer solutions were added to 500 mL water, which was followed by measuring the absorbance of the samples. Ferric chloride, ferrous chloride and alum were dosed from stock solutions to achieve the desired concentrations.

Absorbance measurements were performed with a UV-Vis spectrophotometer (Cary 100 Bio UV-Vis Spectrophotometer, Varian Inc./Aligant Technologies, Canada) using a 1 cm quartz glass cell (Hellma Canada Ltd., Canada).

Figure 19A:
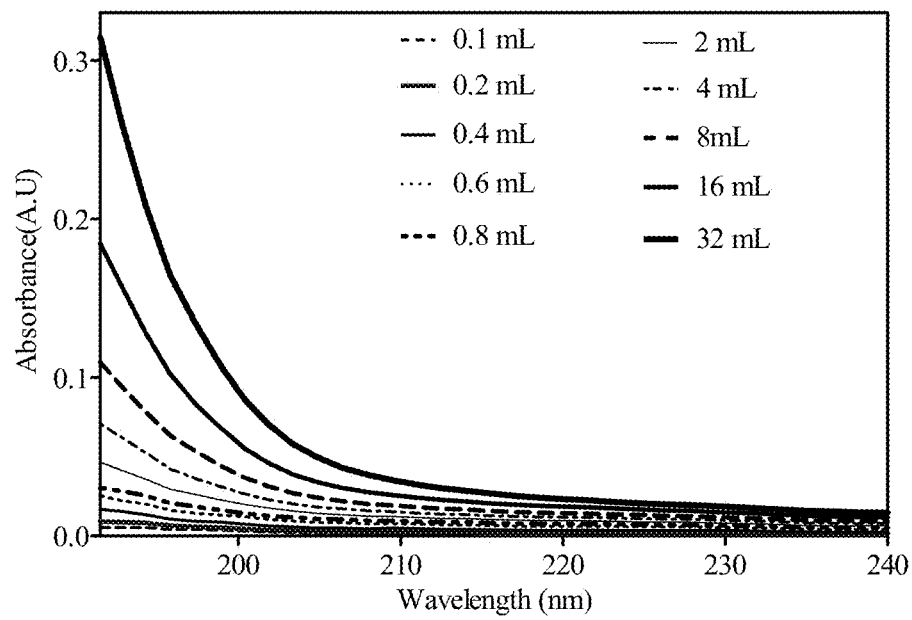
FIG. 19 depicts absorbance scans of Hydrex 6783 polymer (polydiallyldimethyl ammonium chloride (PolyDADMAC)) between 190 nm and 240 nm at a range of polymer concentrations: (a) from 0.1 mL to 32 mL of stock polymer solution (0.053% by weight) in 500 mL of distilled water; and (b) from 0.1 mL to 4 mL of stock polymer solution (0.053% by weight) in 500 mL of distilled water.
Figure 19B:
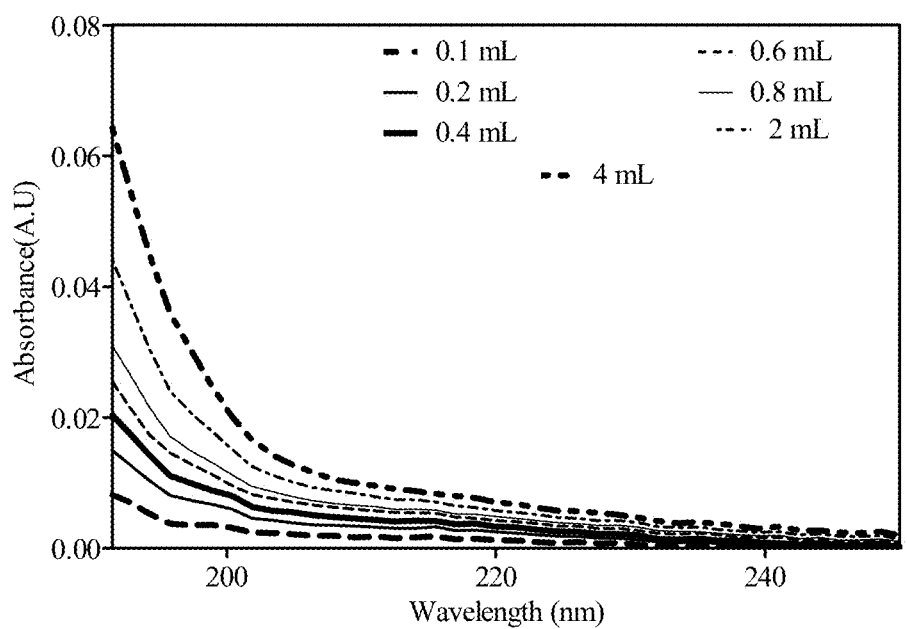
Figure 20A:
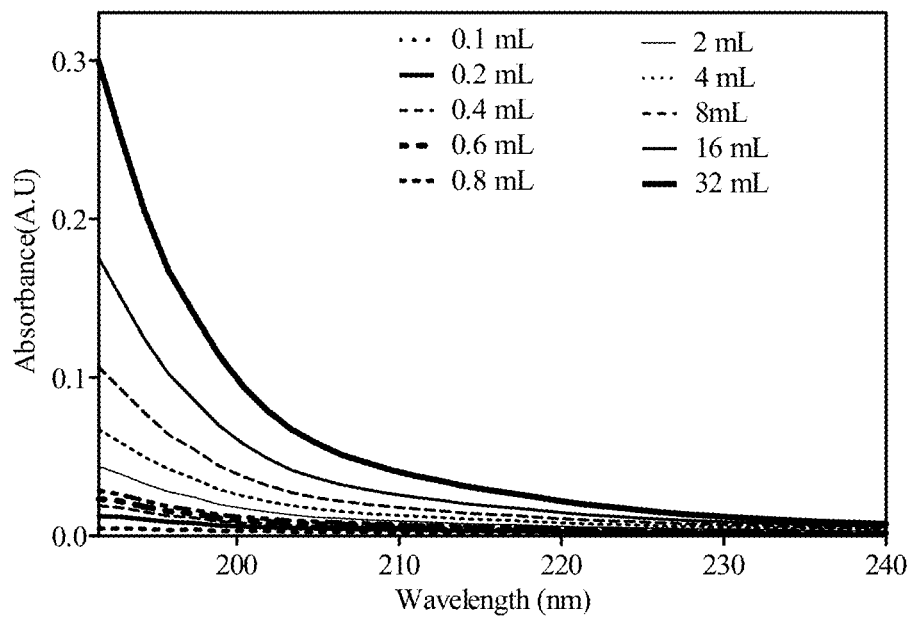
FIG. 20 depicts absorbance scans of Hydrex 6704 polyamine polymer between 190 nm and 240 nm at a range of polymer concentrations: (a) from 0.1 mL to 32 mL of stock polymer solution (0.01% by weight) in 500 mL of distilled water; and (b) from 0.1 mL to 4 mL of stock polymer solution (0.01% by weight) in 500 mL of distilled water.
Figure 20B:
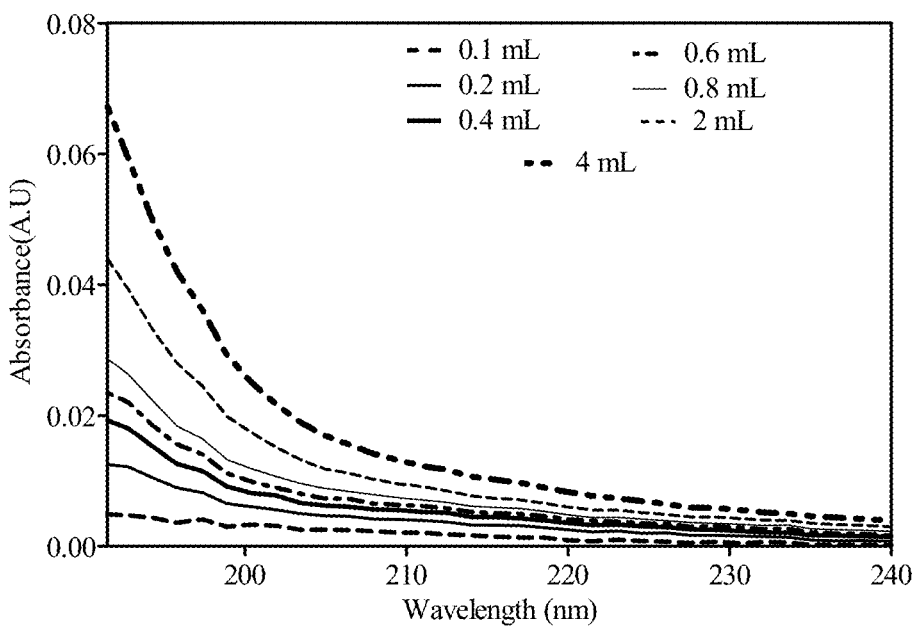
Figure 21:
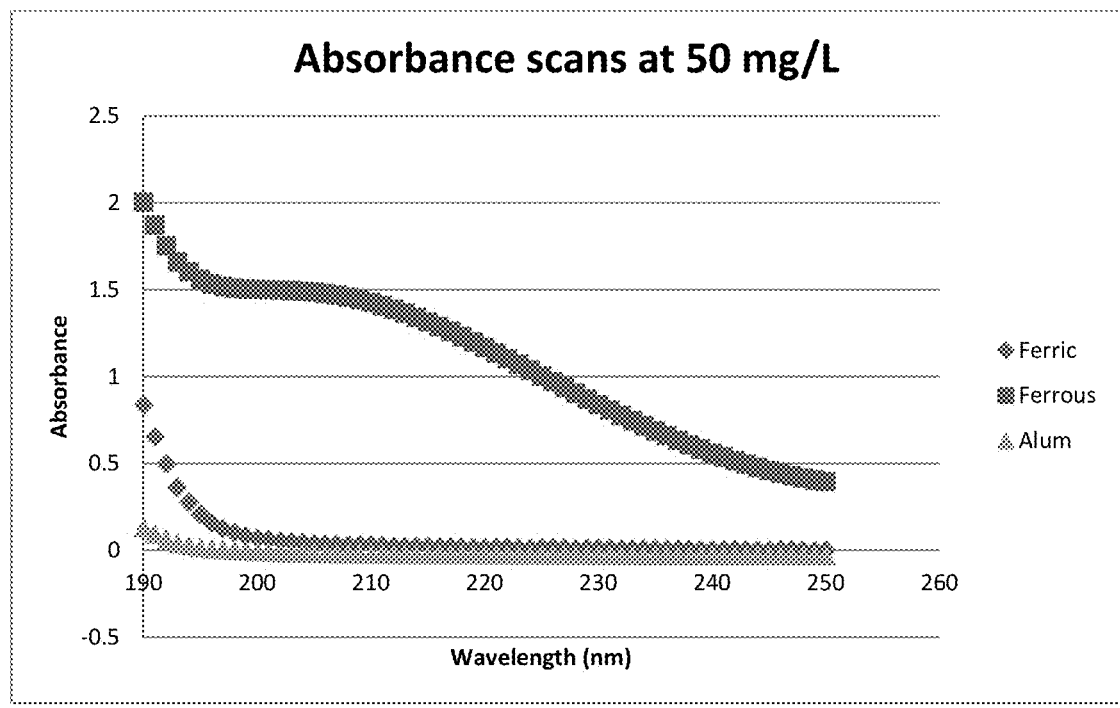
FIG. 21 depicts absorbance scans of ferric chloride, ferrous chloride, and alum between 190 nm and 250 nm at a concentration of 50 mg/L in distilled water.

Absorbance scans of the PolyDADMAC polymer and polyamine polymer between 190 and 240 nm are shown in FIGS. 19 and 20, respectively. FIG. 21 depicts absorbance scans of ferric chloride, ferrous chloride, and alum between 190 nm and 250 nm at a concentration of 50 mg/L in distilled water. For all of these flocculating agents, the highest absorbance was observed at 190 nm.

Figure 22:
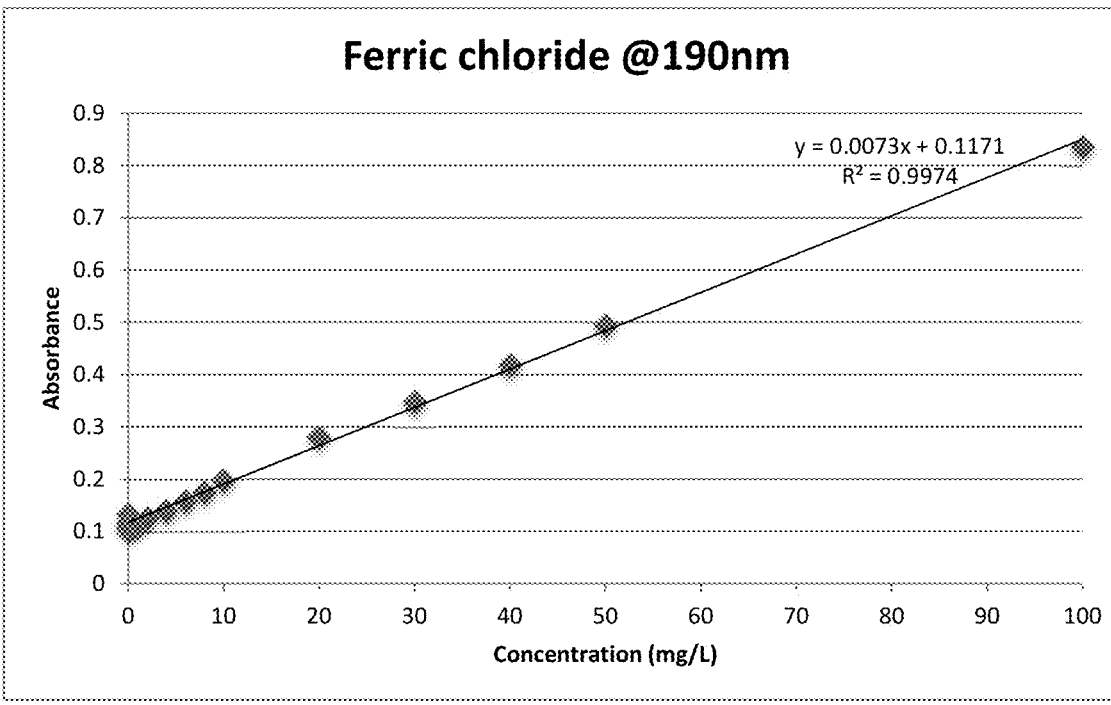
FIG. 22 graphically depicts the relationship between absorbance and concentration for ferric chloride at 190 nm at a concentration range from 0 to 100 mg/L in distilled water.
Figure 23:
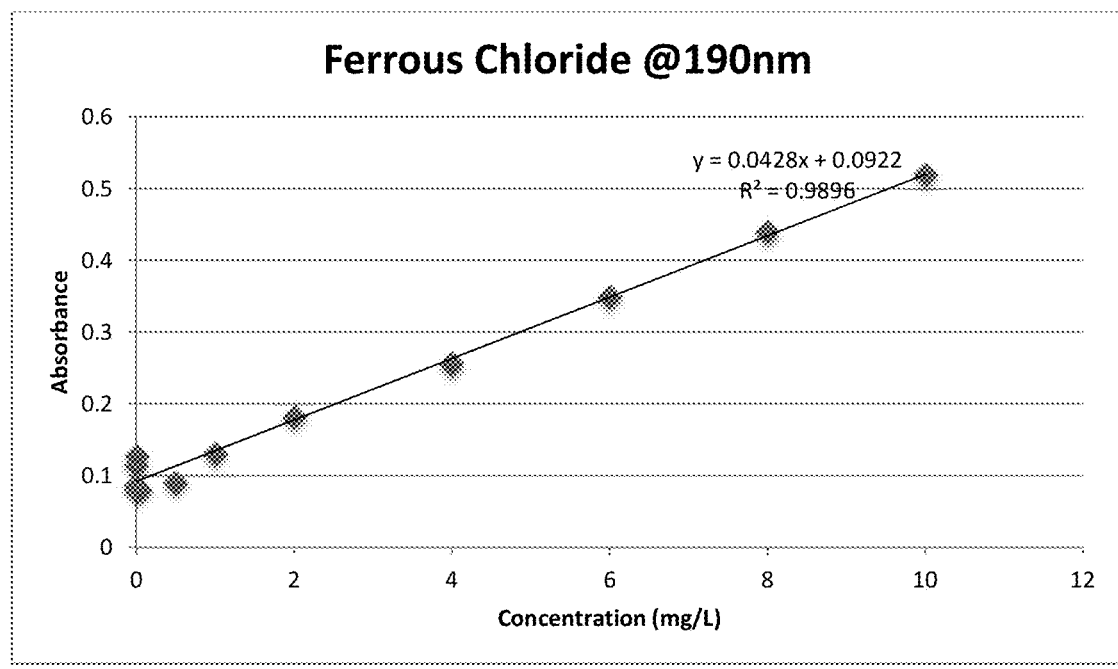
FIG. 23 graphically depicts the relationship between absorbance and concentration for ferrous chloride at 190 nm at a concentration range from 0 to 10 mg/L in distilled water.
Figure 24:
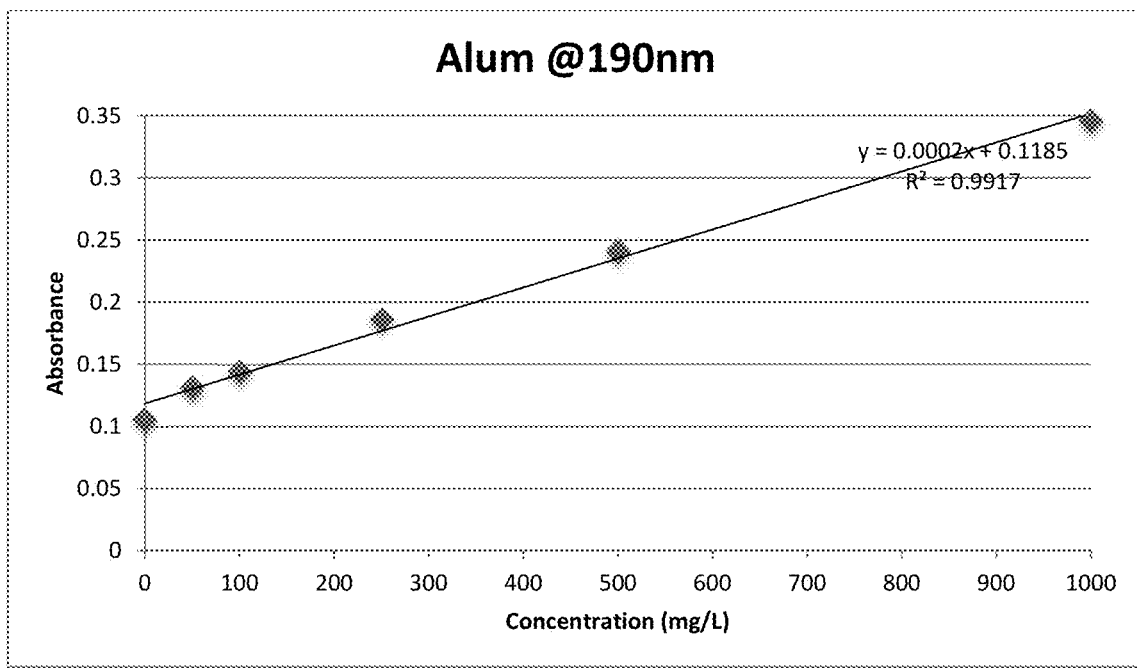
FIG. 24 graphically depicts the relationship between absorbance and concentration for alum at 190 nm at a concentration range from 0 to 1000 mg/L in distilled water.

Plots of absorbance versus concentration at 190 nm for ferric chloride, ferrous chloride, and alum are depicted in FIGS. 22, 23, and 24, respectively.

For all of the flocculating agents tested, a strong linear relationship was established between absorbance values and treatment agent concentrations in the UV-vis range. The incremental increases in flocculating agent concentrations corresponded to incremental increases in absorbance measurements at 190 nm in water for each of the flocculating agents studied.

REFERENCES

Abu Orf, M. M. and Dentel, S. K. 1997. Polymer dose assessment using the streaming current detector. Water Environment Research 69: 1075-1085.

Abu Orf, M. M., Walker, C. A., and Dentel, S. K. 2003. Centrate viscosity for continuous monitoring of polymer feed in dewatering applications. Advances in Environmental Research 7: 687-694.

APHA, American Public Health Association, American Water Works Association, and the Water Environment Federation (1995) *Standard Methods for the Examination of Water and Wastewater.* 19th Ed., Washington, D.C.

Becker, N. S. C., Bennett, D. M., Bolto, B. A., Dixon, D. R., Eldridge, R. J., Le, N. P., and Rye, C. S. 2004. Detection of polyelectrolytes at trace levels in water by fluorescent tagging. Reactive & Functional Polymers 60: 183-193.

Berthouex, P. M. and Brown, L. C. 2002. *Statistics for Environmental Engineers,* $2^{nd}$ Edition. Lewis Publishers, CRC Press, Boca Raton Fla.

Bolto, B. A., 1995. Soluble polymers in water purification. Prog. Polm. Sci., 20: 987-1041.

Byun, S., Kwon, J.-H., Kim, M.-H., Park, K.-Y., and Lee, S. 2007. Automatic control of polymer dosage using streaming potential for waterworks sludge conditioning. Separation and Purification Technology 57: 230-236.

Chadik, P. and Amy G. L. 1983 Removing trihalomethane precursors from various natural waters by metal coagulants. Water Works Assoc., 75(10): 532-536.

Chang, L. L., Bruch, M. D., Griskowitz, N. J. and Dentel, S. K. 2002. NMR spectroscopy for determination of cationic polymer concentrations. Water Research 36: 2255-2264.

Chitikela, S, and Dentel, S. K. 1998. Dual-chemical conditioning and dewatering of anaerobically digested biosolids: Laboratory evaluations. Water Environment Research 70: 1062-1069.

Dentel, S. K. and Abu Orf, M. M. 1995. Laboratory and full-scale studies of liquid stream viscosity and streaming current for characterization and monitoring of dewaterablility. Water Research 29: 2663-2672.

Dentel, S. K., Chang, L. L., Raudenbush, D. L., Junnier, R. W., and Abu-Orf, M. M. 2000. Analysis and Fate of Polymers in Wastewater Treatment. Alexandria, Va.: Water Environment Research Foundation (Publication D00301).

Gehr, R. and Kalluri, R. 1983. The effects of short-term storage and elevated temperatures on the flocculation activity of aqueous polymer solutions. Water Pollution Research Journal of Canada 18: 23-43.

IUPAC Recommendations 1996 in (1996) Pure and Applied Chemistry 68: 2287-2311.

Keenan, H. E., Papavasilopoulos, E. N., and Bache, D. H.1998. Measurement of polymer residuals in an alum sludge. Water Research 32: 3173-3176.

Stuart, B. 2002. *Polymer Analysis*. John Wiley & Sons, West Sussex, England. p. 52-54.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A process for regulating an amount of a flocculating agent added to a process stream comprising:
    (i) determining a desired concentration of a flocculating agent to be added to a process stream, comprising the following steps:
        (a) adding a flocculating agent to a test process stream in a range of amounts;
        (b) obtaining a test sample from the test process stream following addition of each amount of the flocculating agent;
        (c) measuring at least one absorption property of each test sample at a wavelength of about 150 nm to about 240 nm, wherein the at least one absorption property is absorbance or transmittance; and
        (d) when the at least one absorption property is absorbance, plotting the absorbance for each test sample versus the amount of flocculating agent added to the test process stream, wherein adding the flocculating agent to the test process stream in the range of amounts comprises adding the flocculating agent to the test process stream in gradually increasing amounts such that said plotting forms a U-shaped or V-shaped curve, wherein a preselected value for absorbance that corresponds to the desired concentration of the flocculating agent in the process stream corresponds to an absorbance value at or near a minimum in the plot; or
        when the at least one absorption property is transmittance, plotting the transmittance for each test sample versus the amount of flocculating agent added to the test process stream, wherein adding the flocculating agent to the test process stream in the range of amounts comprises adding the flocculating agent to the test process stream in gradually increasing amounts such that said plotting forms an inverted U-shaped or V-shaped curve, wherein a preselected value for transmittance that corresponds to the desired concentration of the flocculating agent in the process stream corresponds to a transmittance value at or near a maximum in the plot; and
    (ii) regulating the amount of the flocculating agent being added to the process stream, comprising the following steps:
        (a) adding the flocculating agent to the process stream, wherein the flocculating agent is the same flocculating agent as used in step (i);
        (b) measuring in-line at least one absorption property of a sample obtained from the process stream at a wavelength of about 150 nm to about 240 nm, wherein the at least one absorption property is absorbance or transmittance, and wherein the wavelength and the at least one absorption property are the same wavelength and at least one absorption property as measured in step (i)(c);
        (c) comparing the measured at least one absorption property of the sample to the preselected value; and
        (d) (I) adjusting the amount of flocculating agent added to the process stream if the measured at least one absorption property is outside a predetermined range around the preselected value, and
            (II) repeating steps (b), (c) and (d)(I) until the measured at least one absorption property of the sample is within a predetermined range around the preselected value, and thereafter maintaining the amount of flocculating agent added to the process stream; or
        (e) maintaining the amount of flocculating agent added to the process stream if the measured at least one absorption property is within a predetermined range around the preselected value;
    wherein step (ii) is automated for real-time regulating of the amount of flocculating agent being added to the process stream;
    wherein the test process stream and the process stream are derived from the same source;
    wherein the process stream comprises suspended particles; and
    wherein the flocculating agent exhibits an absorbance maximum or maxima in the range of from about 150 nm to about 240 nm.

2. The process of claim 1, wherein the process stream is a water-based stream comprising suspended particles; or
    the process stream is from an industrial or treatment process, wherein, optionally, the industrial or treatment process comprises the treatment of: drinking water sources, domestic wastewater, industrial wastewater, a contaminated environmental site, drinking water sludge, domestic wastewater sludge, industrial wastewater sludge, or tailings from gas, oil and mining industries.

3. The process of claim 2, wherein steps (ii)(b), (c), and (d) or (e) are repeated at predetermined intervals during the industrial or treatment process.

4. The process of claim 1, wherein the flocculating agent is:
    i) a synthetic polymer, wherein, optionally, the synthetic polymer is: an (acrylamide)-(dimethylaminoethyl acrylate) copolymer, an (acrylamide)-(chloromethylated dimethylaminoethyl acrylate) copolymer, a polyaminoalkylmethacrylate or copolymer thereof, a polyacrylesteracrylamide copolymer, a polyamine, a polyamidoamine, a polyethyleneimine, a dicyandiamide, a chitosan, a polyacrylamide, a (polyacrylamide)-(carboxylic acid salt) copolymer, a (polyacrylamide)-(sulphonic acid salt) copolymer, a polyethylene oxide, a polyacrylate, an (acrylamide)-(sodium acrylate) copolymer, carboxylmethyl cellulose, a (diallyldimethyl ammonium chloride)-(acrylic acid) copolymer, a (diallyldimethyl ammonium chloride)-(acrylamide) copolymer, an (acrylamide)-(acrylic acid)-(chloromethylated dimethylaminoethyl acrylate) copolymer, polydiallyldimethyl ammonium chloride, a sodium polystyrene sulphonate-based polymer, a sodium polyvinylsulphonate-based polymer, an (acrylic acid)-(2-acrylamido-2-methylpropanesulphonic acid) copolymer, or a mixture thereof;
ii) a biodegradable polymer, wherein, optionally, the biodegradable polymer is a starch-based polymer, or a cellulose-based polymer;
iii) an inorganic conditioner, wherein, optionally, the inorganic conditioner is alum, ferric chloride, ferrous chloride, aluminum perchloride, or lime; or
iv) a mixture thereof.

5. The process of claim 1, wherein the wavelength of step (i)(c) and step (ii)(b) is between about 170 nm and about 240 nm, or between about 170 nm and about 220 nm, or between about 190 and 220 nm.

6. The process of claim 1, further comprising: i) a pretreatment step to remove solid material from each of the test samples and from the sample prior to measuring the at least one absorption property; and/or ii) diluting each of the test samples and the sample prior to measuring the at least one absorption property.

7. A process for monitoring an amount of a flocculating agent added to a process stream comprising:
(i) determining a desired concentration of a flocculating agent to be added to a process stream, comprising the following steps:
(a) adding a flocculating agent to a test process stream in a range of amounts;
(b) obtaining a test sample from the test process stream following addition of each amount of the flocculating agent;
(c) measuring at least one absorption property of each test sample at a wavelength of about 150 nm to about 240 nm, wherein the at least one absorption property is absorbance or transmittance; and
(d) when the at least one absorption property is absorbance, plotting the absorbance for each test sample versus the amount of flocculating agent added to the test process stream, wherein adding the flocculating agent to the test process stream in the range of amounts comprises adding the flocculating agent to the test process stream in gradually increasing amounts such that said plotting forms a U-shaped or V-shaped curve, wherein a preselected value for absorbance that corresponds to the desired concentration of the flocculating agent in the process stream corresponds to an absorbance value at or near a minimum in the plot; or
when the at least one absorption property is transmittance, plotting the transmittance for each test sample versus the amount of flocculating agent added to the test process stream, wherein adding the flocculating agent to the test process stream in the range of amounts comprises adding the flocculating agent to the test process stream in gradually increasing amounts such that said plotting forms an inverted U-shaped or V-shaped curve, wherein a preselected value for transmittance that corresponds to the desired concentration of the flocculating agent in the process stream corresponds to a transmittance value at or near a maximum in the plot; and (ii) monitoring the amount of the flocculating agent being added to the process stream, comprising the following steps:
(a) adding the flocculating agent to the process stream, wherein the flocculating agent is the same flocculating agent as used in step (i);
(b) measuring in-line at least one absorption property of a monitoring sample obtained from the process stream at a wavelength of about 150 nm to about 240 nm, wherein the at least one absorption property is absorbance or transmittance, and wherein the wavelength and the at least one absorption property are the same wavelength and at least one absorption property as measured in step (i)(c);
(c) comparing the measured at least one absorption property of the sample to the preselected value; and
(d) generating a signal if the measured at least one absorption property is outside a predetermined range around the preselected value;
optionally further comprising the following step:
(iii) adjusting the amount of flocculating agent added to the process stream if the measured at least one absorption property is outside the predetermined range around the preselected value;
wherein, when the process includes step (iii), the process optionally further comprises the following steps:
(iv) measuring in-line at least one absorption property of an additional monitoring sample obtained from the process stream at a wavelength of about 150 nm to about 240 nm, wherein the at least one absorption property is absorbance or transmittance, and wherein the wavelength and the at least one absorption property are the same wavelength and at least one absorption property as measured in step (i)(c);
(v) comparing the measured at least one absorption property of step (iv) to the preselected value; and
(vi) maintaining the signal if the measured at least one absorption property of step (iv) is outside the predetermined range around the preselected value;
repeating steps (iii), (iv), (v) and (vi) until the measured at least one absorption property is within the predetermined range around the preselected value; and
ceasing the signal if the measured at least one absorption property is within the predetermined range around the preselected value; or
(vii) ceasing the signal if the measured at least one absorption property of step (iv) is within the predetermined range around the preselected value;
wherein steps (ii)-(vii) are automated for real-time monitoring of the amount of flocculating agent being added to the process stream;
wherein the test process stream and the process stream are derived from the same source;
wherein the process stream comprises suspended particles; and
wherein the flocculating agent exhibits an absorbance maximum or maxima in the range of from about 150 nm to about 240 nm.

8. The process of claim 7, wherein the process stream is a water-based stream comprising suspended particles; or
the process stream is from an industrial or treatment process, wherein, optionally, the industrial or treatment process comprises the treatment of: drinking water sources, domestic wastewater, industrial wastewater, a contaminated environmental site, drinking water sludge, domestic wastewater sludge, industrial wastewater sludge, or tailings from gas, oil and mining industries.

9. The process of claim 7, wherein the flocculating agent is:
   i) a synthetic polymer, wherein, optionally, the synthetic polymer is: an (acrylamide)-(dimethylaminoethyl acrylate) copolymer, an (acrylamide)-(chloromethylated dimethylaminoethyl acrylate) copolymer, a polyaminoalkylmethacrylate or copolymer thereof, a polyacrylesteracrylamide copolymer, a polyamine, a polyamidoamine, a polyethyleneimine, a dicyandiamide, a chitosan, a polyacrylamide, a (polyacrylamide)-(carboxylic acid salt) copolymer, a (polyacrylamide)-(sulphonic acid salt) copolymer, a polyethylene oxide, a polyacrylate, an (acrylamide)-(sodium acrylate) copolymer, carboxylmethyl cellulose, a (diallyldimethyl ammonium chloride)-(acrylic acid) copolymer, a (diallyldimethyl ammonium chloride)-(acrylamide) copolymer, an (acrylamide)-(acrylic acid)-(chloromethylated dimethylaminoethyl acrylate) copolymer, polydiallyldimethyl ammonium chloride, a sodium polystyrene sulphonate-based polymer, a sodium polyvinylsulphonate-based polymer, an (acrylic acid)-(2-acrylamido-2-methylpropanesulphonic acid) copolymer, or a mixture thereof;
   ii) a biodegradable polymer, wherein, optionally, the biodegradable polymer is a starch-based polymer, or a cellulose-based polymer;
   iii) an inorganic conditioner, wherein, optionally, the inorganic conditioner is alum, ferric chloride, ferrous chloride, aluminum perchloride, or lime or
   iv) a mixture thereof.

10. The process of claim 7, wherein the wavelength of step (i)(c), step (ii)(b), and step (iv) is between about 170 nm and about 240 nm, or between about 170 nm and about 220 nm.

11. The process of claim 7, further comprising:
   i) a pretreatment step to remove solid material from each of the test samples, the monitoring sample and the additional monitoring sample prior to measuring the at least one absorption property; and/or
   ii) diluting each of the test samples, the monitoring sample and the additional monitoring sample prior to measuring the at least one absorption property.

* * * * *